US008685963B2

(12) United States Patent
Landry et al.

(10) Patent No.: US 8,685,963 B2
(45) Date of Patent: Apr. 1, 2014

(54) COMPOUNDS THAT INHIBIT NFκB AND BACE1 ACTIVITY

(75) Inventors: Donald W. Landry, New York, NY (US); Shi Xian Deng, White Plains, NY (US); Gangli Gong, Little Neck, NY (US); Yuli Xie, New York, NY (US); Yidong Liu, New York, NY (US); K. Alison Rinderspacher, Bronx, NY (US)

(73) Assignee: The Trustees of Columbia University in the city of New York, New York, NY (US)

( * ) Notice: Subject to any disclaimer, the term of this patent is extended or adjusted under 35 U.S.C. 154(b) by 0 days.

(21) Appl. No.: 13/094,504

(22) Filed: Apr. 26, 2011

(65) Prior Publication Data

US 2012/0064099 A1    Mar. 15, 2012

Related U.S. Application Data

(63) Continuation of application No. PCT/US2009/043011, filed on May 6, 2009.

(60) Provisional application No. 61/143,532, filed on Jan. 9, 2009, provisional application No. 61/143,404, filed on Jan. 8, 2009, provisional application No. 61/109,891, filed on Oct. 30, 2008.

(51) Int. Cl.
*A61K 31/54* (2006.01)
*A01N 43/42* (2006.01)
*A61K 31/47* (2006.01)
*C07D 215/36* (2006.01)

(52) U.S. Cl.
USPC ............... 514/224.5; 514/224.2; 514/311; 546/172

(58) Field of Classification Search
USPC ............... 514/224.5, 224.2, 311; 546/172
See application file for complete search history.

(56) References Cited

U.S. PATENT DOCUMENTS

| 4,253,865 | A | 3/1981 | Chan |
| 4,369,320 | A | 1/1983 | Levitt et al. |
| 5,847,155 | A | 12/1998 | Faraci et al. |
| 6,969,710 | B2 | 11/2005 | Bremberg et al. |
| 2003/0082140 | A1 | 5/2003 | Fisher |
| 2004/0180417 | A1 | 9/2004 | Seidah et al. |
| 2005/0282879 | A1 | 12/2005 | Salehani |
| 2006/0280812 | A1 | 12/2006 | Carlson et al. |
| 2008/0113995 | A1 | 5/2008 | Sorensen et al. |

FOREIGN PATENT DOCUMENTS

| WO | WO/2004/099106 | 11/2004 |
| WO | WO/2008/008463 | 1/2008 |

OTHER PUBLICATIONS

U.S. Appl. No. 12/858,837, Dec. 24, 2012 Non-Final Office Action.
Armstrong et al., "Discovery of Carbohydrate Sulfotransferase Inhibitors from a Kinase-Directed Library", *Angewandte ChemieInternational Edition*, 39(7): 1303-1306, Apr. 3, 2000.
Baraldi et al., "Design, Sythesis, and Biological Evaluation of a Second Generation of Pyrazolo[4,3-e]-1,2,4-triazolo[1,5-c]pyrimidines as Potent and Selective $A_{2A}$ Adenosine Receptor Antagonists", *Journal of Medicinal Chemistry*, 41(12): 2126-2133; Jun. 4, 1998.
Baraldi et al., "7-Substituted 5-amino-2(2-furyl)pyrazolo[4,3-e]-1,2,4-triazolo[1,5-c]pyrimidines as A2A adenosine receptor antagonists: a study on the importance of modifications at the side chain on the activity and solubility", *Journal of Medicinal Chemistry*, 45(1): 115-126, Jan. 3, 2002.
Chang et al., "Synthesis and application of functionally diverse 2,6,9,-trisubstituted purine libraries as CDK inhibitors", *Chemistry & Biology*, 6(6): 361-375, Jun. 1999.
Chang et al., "Purine-based inhibtors of inositol-1,4,5,-trisphosphate-3-kinase", *Chembiochem,*, 3(9): 897-901, Sep. 2, 2002.
Cirrito et al., "In Vivo Assessment of Brian Interstitial Fluid with Microdialysis Reveals Plaque-Associated Changes in Amyloid-β Metabolism and Half-Life", *The Journal of Neuroscience*, 23(26): 8844-8853, Oct. 1, 2003.
Clarkson et al., "NF-κκB Inhibits Apoptosis in Murine Mammary Epithelia", *The Journal of Biological Chemistry*, 275(17): 12737-12742, Apr. 2000.
Cogswell et al., "Selective activation of NF-κB submits in human breast cancer: potential roles for NF-κB2/p52 and for Bcl-3", *Oncogene*, 19: 1123-1131, 2000.
Gangjee et al., "Deisgn, synthesis, and biological activities of classical N-[4-[2-(2-amino-4-ethylpyrrolo[2,3-d]pyrimidin-5-yl)ebethyl]benzoyl]-1-glutamie acid and its 6-methyl derivative as potential dual inhibitors of thymidylate synthase and dihydrofolate reductase and as potential antitumor agents", *Jounral of Medicinal Chemistry*, 46(4): 591-600, Feb. 13, 2003.
Glowa et al., "Effects of dopamine reuptake inhibitors on food-and cocaine-maintained responding: I. Depedence on unit dose of cocaine", *Experimental and Clinical Psychopharmacology*, 3(3):219-231, 1995.
Hussain et al., "Identification of a novel aspartic protease (Asp2) as beta-secretase", *Molecular Cell Neuroscience*, 14(6): 419-427, Dec. 1999.

(Continued)

*Primary Examiner* — Sreeni Padmanabhan
*Assistant Examiner* — Uma Ramachandran
(74) *Attorney, Agent, or Firm* — Baker Botts, L.L.P.

(57) ABSTRACT

The present invention relates to compounds with activity as BACE1 and NFκB modulators, and methods for treating, preventing, or ameliorating neurodegenerative diseases, such as Alzheimer's disease. The present invention is also directed to the treatment of diseases related to dysfunction of cell proliferation, the immune system and/or inflammation using such compounds or pharmaceutical compositions containing such candidate compounds.

4 Claims, 16 Drawing Sheets

(56) References Cited

OTHER PUBLICATIONS

Hussain et al., "Oral administration of a potent and selective non-peptidic BACE-1 inhibitor decreases β-cleavage of amyloid precursor protein and amyloid-β production in vivo", *Journal of Neurochemistry*, 100: 802-809, 2007.

Karin, "The Beginning of the End: IκB Kinase (IKK) and NF-κb Activation", *The Journal of Biological Chemistry*, 274(39): 27339-27342, Sep. 1999.

Khersonsky et al., "Facilitated forward chemical genetics using a tagged triazine library and zebrafish embryo screening", *Journal of the American Chemical Society*, 125(39): 11804-11805, Oct. 1, 2003.

Kumar et al., "Nuclear factor-κB: its role in health and disease", *Journal of Molecular Medicine*, 82(7):434-448 (2004).

Lam et al., "Small Molecule Inhibitors of IκB Kinase are Selectively Toxic for Subgroups of Diffuse Large B-Cell Lymphoma Defined by Gene Expression Profiling", *Clinical Cancer Research*, 11: 28-40, Jan. 21, 2005.

Matecka, et al., "Development of novel, potent, and selective dopamine reuptake inhibitors through alteration of the piperazine ring of 1-[2-(diphenylmethoxy)ethyl]- and 1-[2-[Bis(4-fluorophenyl)methoxy]ethyl]-4-(3-phenylpropyl)piperazines (GBR 12935 and GBR 12909)", *J. Med. Chem.*, 139:4704-4716, 1996.

Matsugi et al., "Doebner-Miller synthesis in a two-phase system: practical preparation of quinolines", *Tetrahedron Letters*, 41: 8523, 2000.

May et al., "Selective inhibition of NF-κB activation by a peptide that blocks the interaction of NEMO with the IκB kinase complex", *Science*, 289(5484): 1550-1554, Sep. 2000.

May et al., "Characterization of the IκB kinase NEMO binding domain", *The Journal of Biological Chemistry*, 277(48): 45992-6000, Nov. 2002.

Mayer et al., "Cell-based assays using primary endothelial cells to study multiple steps in inflammation", *Methods Enzymol*, 414: 266-283, 2006.

Nakshatri et al., "Constitutive Activation of NF-κB during Progression of Breast Cancer to Hormone-Independent Growth", *Molecular and Cellular Biology*, 17(7): 3629-3639, Jul. 1997.

Newton et al., "Negative Regulation of Transactivation Function but Not DNA Binding of NF-κB and AP-1 by IκBβ1 in Breast Cancer Cells", *The Journal of Biological Chemistry*, 274(26): 18827-18835, Jun. 1999.

Ngo et al., "A loss-of-function RNA interference screen for molecular targets in cancer", *Nature*, 441(7089): 106-110, May 2006.

Noraberg et al., "Organotypic hippocampal slice cultures for studies of brain damage, neuroprotection and neurorepair", *Curr Drug Targets CNS Neuraol Disord.*, 4(4): 435-52, Aug. 2005.

Paris, et al., "Inhibition of Aβ production by NF-κB inhibitors", *Neuroscience Letters*, 415(1):11-16 (2007).

Park, et al., "Metabolism of Flourine-Containing Drugs", *Annu. rev. Pharmacol. Toxicol.*, 141:443-470, 2001.

Patel et al., "Paclitaxel sensitivity of breast cancer cells with constitutiveky active NF-κB is enhanced by IκBα super-repressor and parthenolide", *Oncogene*, 19(36): 4159-4169, 2000.

Pomerantz et al., "Two Pathways to NF-κB", *Molecular Cell*, 10(4): 693-695, Oct. 2002.

Poulaki et al., "Constitutive Nuclear Factor- κB Activity is Crucial for Human Retinoblastoma Cell Viability", *Am J. Pathol*, 161(6): 2229-2240, Dec. 2002.

Ritchie et al., "Metal-Protein attenuation with iodochlorhydroxyquin (Clioquinol) targeting Aβ amyloid eposition and toxicity in Alzheimer disease: A pilot phase 2 clinical trial", *Arch Neural*, 60(12):1685-1691, 2003.

Rosania et al., "Myoseverin, a microtubule-binding molecule with novel cellular effects", *Nature Biotechnology*, 18(3): 304-308, Mar. 2000.

Santoro et al., "NF-κB and virus infection: who controls whom", *The EMBO Journal*, 22(11): 2552-2560, 2003.

Segev et al., "Müllerian Inhibiting Substance Inhibits Breast Cancer Cell Growth through an NFκB-mediated Pathway", *The Journal of Biological Chemistry*, 275(37): 28371-28379, Sep. 2000.

Selkoe, "Alzheimer's Disease: Genes, Proteins, and Therapy", *Physiological Reviews*, 81(2): 741-766, Apr. 2001.

Senftleben et al., "Activation by IKKα of a second, evolutionary conserved, NF-κB signaling pathway", *Science*, 293(5534): 1495-1499, Aug. 2001.

Sinha et al., "Purification and cloning of amyloid precursor protein beta-secretase from human brain", *Nature*, 402(6761): 537-540, Dec. 2, 1999.

Sovak et al., "Aberrant Nuclear Factor-κB/Rel Expression and the Pathogenesis of Breast Cancer", *The American Society for Clinical Investigation*, 100(12): 2952-2960, Dec. 1997.

Sovak et al., "The Inhibitory Effects of Transforming Growth Factor β1 on Breast Cancer Cell Proliferation Are Mediated through Regulation of Aberrant Nuclear Factor-κB/Rel Expression)", *Cell Growth & Differentiation*, 10(8): 537-544, Aug. 1999.

Vassar et al., "β-secretase cleavage of Alzheimer's amyloid precursor protein by the transmembrane aspartic protease BACE", *Science*, 286(5440): 735-741, Oct. 22, 1999.

Vassar, "β-Secretase (BACE) as a drug target for alzheimer's disease", *Advanced Drug Delivery Reviews*, 54(12): 1589-1602, Dec. 7, 2002.

Verdugo et al., "Discovery of estrogen sulfotransferase inhibitors from a purine library screen", *Journal of Medicinal Chemistry,*, 44(17): 2683-2686, Aug. 16, 2001.

Yan et al., "Membrane-anchored aspartyl protease with Alzheimer's disease beta-secretase activity", *Nature*, 402(6761): 533-537, Dec. 2, 1999.

Zhou et al., "HER-2/neu Blocks Tumor Necrosis factor-induced Apoptosis via the Akt/NF-κB Pathway", *The Journal of Biological Chemistry*, 275(11): 8027-8031, Mar. 2000.

U.S. Appl. No. 12/858,837 (US20110071124), filed Aug. 18, 2010 (Mar. 24, 2011).

International Search Report for PCT/US2009/43009, dated Oct. 22, 2009.

International Search. Report for PCT/US2009/43011, dated Aug. 13, 2009.

Aggarwal, "Nuclear factor-κB: a transcription factor for all seasons", *Expert Opin. Ther. Targets*, 11(2):109-110 (2007).

Austin et al., "NIH Molecular Libraries Initiative", *Science*, 306: 1138-1139 (Nov. 12, 2004).

D'Acquisto et al., "From willow bark to peptides: the ever widening spectrum of NF-κB inhibitors", *Current Opinion Pharmacology.*, 6: 387-392 (Jun. 14, 2006).

Davis et al., "A Cell-Based Assay for IκBα Stabilization Using a Two-Coir Dual Luciferase-Based Sensor", *Assay and Drug Development Technologies.*, 5(1): 85-103 (2007).

Davis et al., "Constitutive Nuclear Factor κB Activity is Required for Survival of Activated B Cell-like Diffuse Large B Cell Lymphoma Cells", *Journal of Experimental Medicine*, 194(12): 1861-1874 (Dec. 17, 2001).

Feng et al., "A High-Throughput Screen for Aggregation-Based Inhibition in a Large Compound Library", *J. Med Chem.*, 50: 2385-2390 (2007).

Ferrell, "Why do protein kinase cascades have more than one level?" *TiBS*, 22: 288-289 (Aug. 1997).

Gilmore, "Introduction to NF-κB: players, pathways, perspectives", *Oncogene*, 25: 6680-6684 (2006).

Gilmore et al., "Inhibitors of NF-κB Signalling: 785 and counting", *Oncogene*, 25: 6687-6899 (2006).

Hoffman et al., "Transcriptional regulation via the NF-κB signalling module", *Oncogene*, 25: 6706-6716 (2006).

Izban et al., "Constitutive Expression of NF-κB is a Characteristic Feature of Mycosis Fungoides: Implications for Apoptosis Resistance and Pathogenesis" *Human Pathology*, 31(12): 1482-1490 (Dec. 2000).

Kamthong et al., "Inhibitor of nuclear factor-κB induction by cAMP antagonizes interleuki-1-induced human macrophage-colony-stimulating-factor expression", *Biochem. J.*, 356: 525-530 (2001).

(56) References Cited

OTHER PUBLICATIONS

Lee et al., "Selective Inhibitors of the Proteasome-dependent and Vacuolar Pathways of Protein Degradation in Saccharomyces cerevisiae*" *The Journal of Bilogical Chemistry*, 271(44): 27280-27284 (1996).

Okamoto et al., "NF-κB Signalling and Carcinogenesis", *Current Pharmaceutical Design*, 13: 447-462 (2007).

Palanki et al., "The Design and Synthesis of Novel Orally Active Inhibitors of AP-1 and NF-κB Mediated Transcriptional Activation. SAR of in Vitro and in Vivo Studies", *Bioorganic & Medicinal Chemistry Letters*, 13: 4077-4080 (2003).

Perkins, "Integrating cell-signalling pathways with NF-κB and IKK function", *Nature Reviews Molecular Cell Biology*, 8: 49-62 (Jan. 2007).

Pierce et al., "Novel Inhibitors of Cytokine-induced IκBα Phosphorylation and Endothelial Cell Adhesion Molecule Expression Show Anti-inflammatory Effects in Vivo", *The Journal of Biological Chemistry*, 272(34): 21096-21103 (1997).

Sen et al., "Inducibility of κ Immunoglobulin Enhancer-Binding Protein NF-κB by a Posttranslational Mechanism", *Cell*, 47: 921-928 (Dec. 26, 1986).

Shoichet, "Interpreting Steep Dose-Response Curves in Early Inhibitor Discovery" *J. Med. Chem.*, 49: 7274-7277 (2006).

Xie et al., "Convenient preparation of N-8-quinolinyl benzenesultams as novel NF-κB inhibitors", ScienceDirect, *Tetrahedron Letters* 49: 2320-2323 (2008).

Xie et al., "Identification of N-(quinolin-8-yl) benzenesulfonamides as agents capable of down-regulating NFκB activity within two separate high-throughput screens of NFκB activation", *Bioorganic & Medicinal Chemistry Letters*, 18: 329-335 (2008).

U.S. Appl. No. 12/858,837, Oct. 7, 2013 Final Office Action.

General structure of *N*-(quinolin-8-yl)benzenesulfonamide open chain structure.

General structure of *N*-(quinolin-8-yl)benzenesulfonamide cyclized structure.

The one-pot synthesis of compound 1a.

Synthesis of quinazolines of 9i-k by Skraup reaction.

9i R¹ = CH₃, R² = H, R³ = H
9j R¹ = H, R² = CH₃, R³ = H
9k R¹ = H, R² = H, R³ = CH₃

The one-pot synthesis of N-8-quinolinyl benzenesultams.

| Comp | R¹ | R² | R³ | R⁴ | R⁵ | R⁶ | R⁷ | R⁸ | R⁹ | Yield(%) |
|------|-----|-----|-----|-----|------|-----|-----|------|-----|----------|
| 1a | CH₃ | H | H | H | OCH₃ | H | H | CH₃ | H | 78 |
| 1b | H | H | H | H | H | H | H | OCH₃ | H | 76 |
| 1c | H | H | H | H | H | H | H | CF₃ | H | 81 |
| 1d | H | H | H | H | H | H | H | Cl | H | 79 |
| 1e | H | H | H | H | H | H | H | CH₃ | H | 95 |
| 1f | CH₃ | H | H | H | H | H | H | F | H | 75 |
| 1g | CH₃ | H | H | H | H | H | H | OCH₃ | H | 70 |
| 1h | CH₃ | H | H | H | H | H | H | CF₃ | H | 91 |
| 1i | CH₃ | H | H | H | H | H | H | H | H | 90 |
| 1j | H | CH₃ | H | H | H | H | H | H | H | 77 |
| 1k | H | H | CH₃ | H | H | H | H | H | H | 79 |
| 1l | H | H | H | Cl | H | H | H | H | H | 73 |
| 1m | H | H | H | H | H | H | H | F | H | 84 |
| 1n | H | H | H | H | H | H | Cl | H | H | 80 |
| 1o | H | H | H | H | H | H | CH₃ | H | H | 72 |
| 1p | H | H | H | H | H | H | H | H | Cl | 75 |

Table 1. SAR surrounding the N-(quinolin-8-yl)benzenesulfonamides

| Control compound # | | | | IκBα stabilization EC50 (µM) and efficacy[a] | IκBα stabilization EC50 (µM) ratio[b] | Translocation of NFκB IC50[c] (µM) | NFκB-bla IC50 (µM) | Cytotoxicity IC50 (µM) |
|---|---|---|---|---|---|---|---|---|
| 1 | | | | 1.0, 100% | 5.2, 100% | ND | 0.6 | >10 |
| 2 | | | | NA | NA | 3.0 | ND | ND |
| 3 | | | | Inactive | Inactive | Inactive | 2 | Inactive |

| Analogue # | R | R' | R'' | | | | | |
|---|---|---|---|---|---|---|---|---|
| 4 | Phenyl | H | H | 17, 350% | 20 | >10 | 8.0 | Inactive |
| 6 | 4-Nitrophenyl | H | H | 6.5, 560% | 17 | 1.5 | 5.0 | Inactive |
| 7 | 2-Nitrophenyl | H | H | 11, 620% | 12 | 3.2 | 10 | Inactive |
| 8 | 2-Nitrophenyl | H | Me | 6.8, 200% | 8.0 | 3.8 | 6.0 | Inactive |
| 9 | 3-Nitrophenyl | H | Me | 6.0, 110% | 13 | 0.9 | 1.0 | >57 |
| 10 | 4-Methyl-2-nitrophenyl | H | H | 6.8, 275% | 10 | 2.1 | 6.0 | >57 |
| 11 | 2-Methyl-5-nitrophenyl | H | H | 1.0, 18% | >10 | 1.6 | 1.8 | >57 |
| 12 | 2-Nitro-4-(trifluoromethyl)phenyl | H | Me | 3.6, 200% | 20 | 3.7 | 1.3 | >57 |
| 13 | 2-Nitro-4-(trifluoromethyl)phenyl | H | Me | 10, 50% | 3.6 | 1.1 | 13 | >57 |
| 14 | 4-Methyl-2-nitrophenyl | H | Me | 6.8, 60% | 7.6 | 2.1 | 4.0 | >57 |
| 15 | 4-Methoxy-2-nitrophenyl | OMe | Me | ND | ND | 1.0 | ND | ND |
| 16 | 2-Methyl-5-nitrophenyl | H | Me | >20 | >57 | Inactive | >57 | Inactive |
| 17 | 2-Methyl-2-nitrophenyl | OMe | Me | >10 | >57 | Inactive | Inactive | >57 |
| 18 | 4-Methyl-2-nitrophenyl | OMe | Me | 20, 150% | 20 | >10 | >57 | >57 |
| 19 | 4-Methylphenyl | H | Me | 11, 300% | 8.5 | 2.0 | 13.5 | Inactive |
| 20 | 2-Aminophenyl | H | Me | 8.0, 250% | 8.0 | 2.8 | 5.5 | >57 |
| 21 | 2-Aminophenyl | OMe | H | 4.0, 90% | 4.0 | 1.0 | 2.0 | >57 |
| 22 | 2-Amino-4-methyl phenyl | OMe | Me | 9.4, 23% | 3.0 | 3.6 | >57 | Inactive |
| 23 | 2-Amino-4-methyl phenyl | OMe | Me | 5.3, 250% | 9.0 | 1.3 | 7.0 | Inactive |
| 24 | Thiophen-2-yl | H | H | 2.7, 190% | 2.7 | 1.1 | 1.0 | >57 |
| 25 | 5-Chlorothiophen-2-yl | H | H | 5.9, 170% | 6.8 | 1.0 | 3.4 | Inactive |
| 26 | 5-Bromothiophen-2-yl | H | Me | 1.4, 60% | 2.1 | 1.3 | 1.3 | >10 µM |
| 27 | 5-Chlorothiophen-2-yl | H | Me | 6.1, 22% | 6.4 | 1.4 | 5.0 | >57 |

[a] EC50 values from the IκBα stabilization assay shown for the green luminescence reporter along with the % efficacy.
[b] EC50 values from the ratio of the green and red luminescent values for the IκBα stabilization. Data are averages from two to three experiments where each experiment consisted of concentration-titration for each compound performed in duplicate and fitting concentration-response curves to the response after bioassay. NA, not applicable; the compound only showed a strong inhibitory response in the original qHTS (IC50 = 2.5 µM, 95% inhibition) in the non-specific (red luminescence) dataset.
[c] IC50 values are derived from curve-fitting to data from a single experiment performed in triplicate. ND, not determined. All compounds showed >90% efficacy in the translocation assay except compounds 15 (78%) and 27 (75%). The cytotoxicity assay was performed in CCl-Ly3 cells using a 4 h endpoint.

FIG. 7A

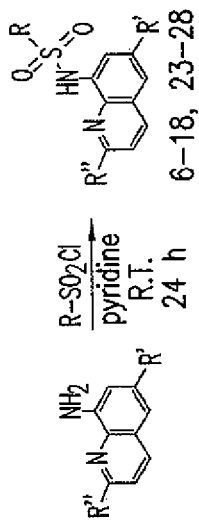

FIG. 7B

Table 2. SAR surrounding the C7-locked N-(quinolin-8-yl)benzenesulfonamides

| Analogue # | R | R' | R'' | R''' | IkBα stabilization EC50 (μM) and efficacy[a] | IkBα stabilization EC50 (μM) ratio[b] | Translocation of NFκB IC50[c] (μM) | NFκB-bla IC50 (μM) | Cytotoxicity IC50 (μM) |
|---|---|---|---|---|---|---|---|---|---|
| 5 | H | H | H | H | 2.2, 120% | 2.6 | 1.0 | 3.4 | Inactive |
| 28 | H | H | H | OH | ND | ND | Inactive | ND | ND |
| 29 | H | H | H | OMe | 1.3, 20% | 1.4 | 1.0 | 1.3 | Inactive |
| 30 | H | H | H | Me | 0.5, 60% | 0.8 | 0.6 | 0.8 | >57 |
| 31 | H | H | H | CF3 | 0.7, 32% | 1.0 | 1.0 | 1.2 | Inactive |
| 32 | H | H | OMe | Me | 1.3, 34% | 1.6 | 1.2 | 2.0 | Inactive |
| 33 | H | H | H | F | 4.1, 122% | 12 | 1.7 | 1.8 | Inactive |
| 34 | H | H | H | Cl | 1.1, 66% | 11 | 1.1 | 1.9 | Inactive |
| 35 | H | OMe | H | H | ND | ND | 2.5 | ND | ND |
| 36 | H | Me | H | H | 7.0, 32% | 10 | ND | 8.1 | Inactive |
| 37 | Me | H | OMe | Me | 1.4, 300% | 2.3 | 0.9 | 1.1 | >57 |
| 38 | Me | H | H | OH | 8.0, 120% | 11 | 10 | 6.7 | >57 |
| 39 | Me | H | H | OMe | 3.7, 200% | 3.4 | 2.5 | 3.2 | >57 |
| 40 | Me | H | H | CF3 | 8.9, 700% | 7.2 | 1.2 | 3.6 | Inactive |

FIG. 7C

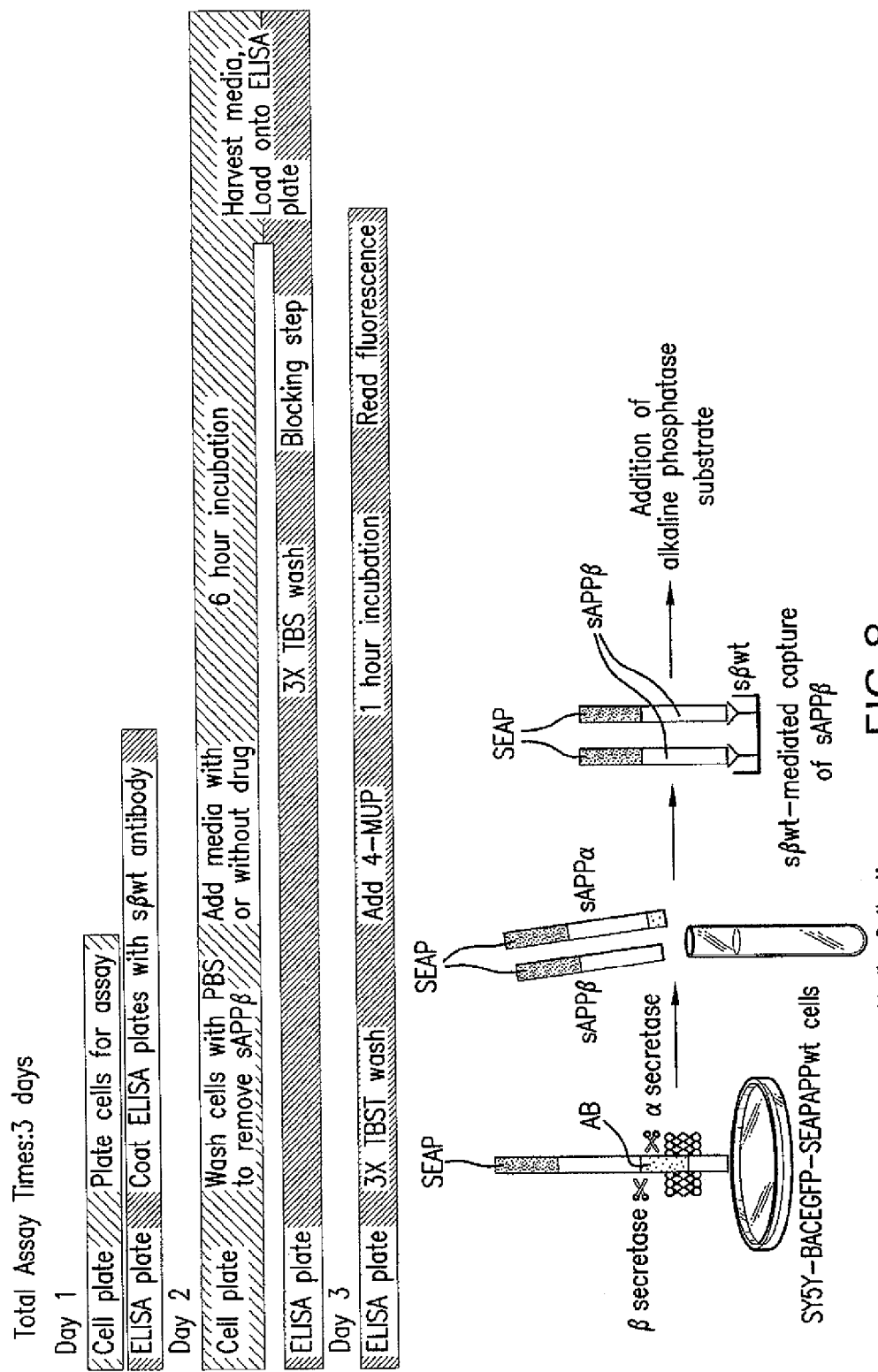

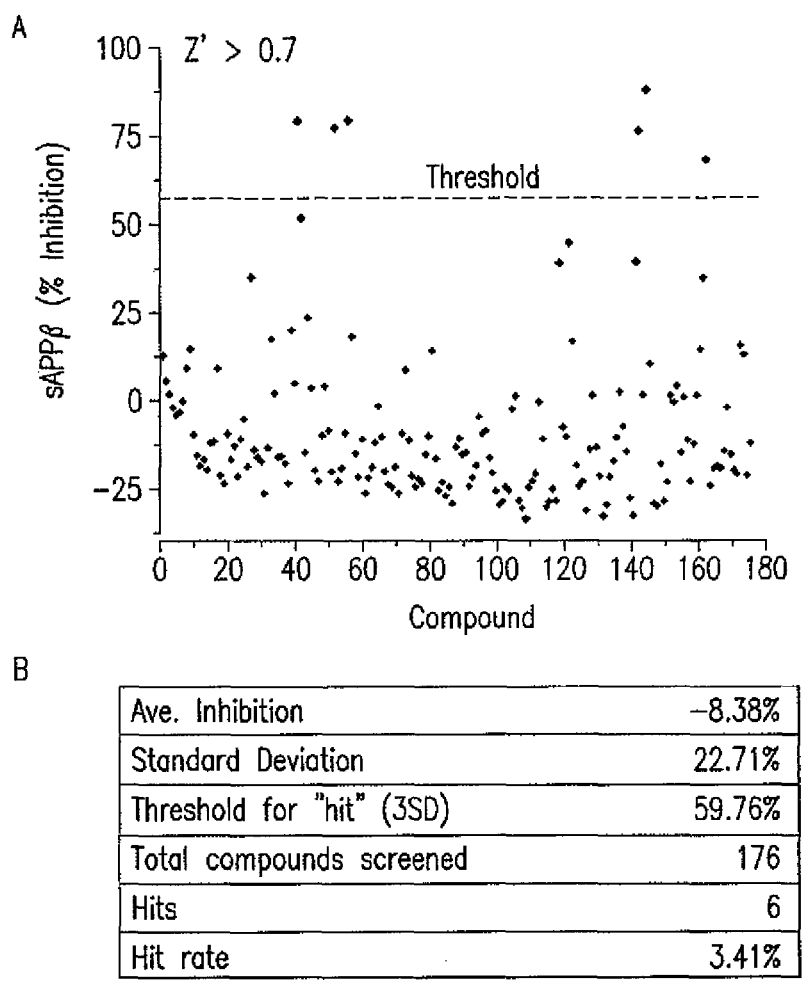

Targeted screen N-(quinolin-8-yl)benzenesulfonamides. Based on their inhibitory activity on NF-kB and structural similarity to two compounds under investigation in AD clinical trials as well as to numerous hits from the primary screen of LDDN compounds, we conducted a small-scale screen using 176 structurally-related compounds based on the scaffold of N-(quinolin-8-yl) benzenesulfonamides. A) Primary screen was conducted in 96-well format at 2 µM concentration in duplicate. Data points represent mean of two determinations. The Z' factors for the four 96-well plates used in the screen were all above 0.7. B) Statistics from the primary screen. The threshold value for hit selection was set at 3 standard deviations, or 59.76%, yielding 6 hit compounds and a hit rate of 3.41%.

FIG.9

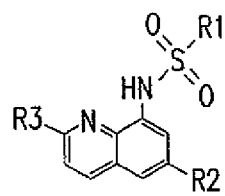

| Compound | R1 | R2 | R3 | IC$_{50}$ (sAPP$\beta$) ($\mu$M) |
|---|---|---|---|---|
| CU-131 | 1-naphthalene | H | H | 6.46 |
| CU-138 | 1-naphthalene | Br | H | 9.51 |
| CU-150 | 2-thiophene | H | H | 8.03 |
| CU-151 | 4-methoxyphenyl | H | H | 5.92 |
| CU-152 | 4-nitrophenyl | H | H | 4.63 |
| CU-153 | 2-nitrophenyl | H | H | 1.58 |
| CU-155 | 2-naphthalene | H | H | 2.20 |
| CU-156 | 8-quinoline | H | H | 4.23 |
| CU-163 | 2-naphthalene | Br | H | 0.79 |
| CU-166 | phenyl | Br | H | 13.45 |
| CU-167 | 4-methylphenyl | Br | H | 1.09 |
| CU-168 | 8-quinoline | Br | H | 17.17 |
| CU-225 | 4-methylphenyl | H | Me | 3.79 |
| CU-242 | 2-aminophenyl | H | H | 3.82 |
| CU-261 | 4-methoxy-2-nitrophenyl | H | H | 1.92 |
| CU-264 | 4-trifluoromethyl-2-aminophenyl | H | H | 0.53 |
| CU-265 | 4-trifluoromethyl-2-nitrophenyl | H | H | 2.95 |
| CU-268 | 2-nitrophenyl | OMe | H | 8.11 |
| CU-271 | 4-methoxy-2-aminophenyl | H | H | 2.74 |
| CU-273 | 2-nitrophenyl | H | Me | 12.43 |
| CU-274 | 2-aminophenyl | H | Me | 11.11 |
| CU-278 | 4-methoxy-2-aminophenyl | H | Me | 11.48 |
| CU-280 | 4-trifluoromethyl-2-nitrophenyl | H | Me | 5.51 |
| CU-281 | 4-trifluoromethyl-2-aminophenyl | H | Me | 3.28 |
| CU-294 | 2-naphthalene | OMe | H | 3.75 |
| CU-295 | 1-naphthalene | OMe | H | 3.63 |

FIG.10A

| Compound | Structure | IC$_{50}$ (sAPP$\beta$) ($\mu$M) |
|---|---|---|
| CU-262 | 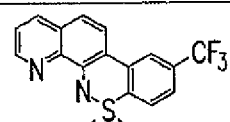 | 0.82 |
| CU-282 | 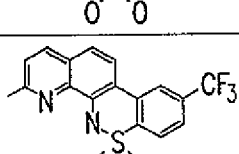 | 1.11 |

SAR studies of *N*-(quinolin-8-yl) benzenesulfonamides. 28 full and partial hits from the targeted screen of *N*-(quinolin-8-yl) benzenesulfonamides were characterized in SY5Y-BACEGFP-SEAPAPPwt cells using the cell-based BACE1 assay. All compounds were tested at 8 concentrations (30, 10, 3, 1, 0.3, 0.1, 0.03, and 0.01 $\mu$M), and data points were analyzed with Origin software and fitted using a logistic model for IC$_{50}$ determination.

FIG. 10B

Immunocytochemistry of primary cortical neurons. DIV-14 primary cortical neurons from wild-type mice were fixed, permeabilized, and stained with TUJ1 to visualize neuronal β-tubulin (green). Cell nuclei (blue) were visualized with a DAPI co-stain. Cells were imaged with the Nikon C1 digital confocal system at 60X magnification.

US 8,685,963 B2

COMPOUNDS THAT INHIBIT NFκB AND BACE1 ACTIVITY

CROSS-REFERENCE TO RELATED APPLICATIONS

The present application is a continuation of International Application No. PCT/US2009/043011, filed May 6, 2009 and published in English as WO2010/051064 on May 6, 2010, which claims the priority benefits of U.S. Provisional Application No. 61/109,891, filed Oct. 30, 2008; U.S. Provisional Application No. 61/143,404, filed Jan. 8, 2009; and U.S. Provisional Application No. 61/143,532, filed Jan. 9, 2009, all four of which are hereby incorporated by reference in their entireties.

GRANT INFORMATION

This invention was made with government support under grants P50 AG08702, and 5RO1 AT001643 awarded by the National Institutes of Health, the Molecular Libraries Initiative of the National Institutes of Health Roadmap for Medical Research and the Intramural Research Program of the National Human Genome Research Institute, National Institutes of Health. The government has certain rights in the invention.

1. INTRODUCTION

The present invention relates to compounds with activity as NFκB inhibitors. The present invention also relates to methods for treating, preventing, and/or ameliorating diseases related to dysfunction of cell proliferation, the immune system, inflammation and/or neurodegeneration using such compounds or pharmaceutical compositions comprising such compounds.

2. BACKGROUND OF THE INVENTION

Nuclear factor-κ B (NFκB) signaling is an essential signal transduction pathway involved in inflammatory responses, oncogenesis, viral infection, the regulation of cell proliferation and apoptosis and, in particularly in the case of B and T lymphocytes, in antigenic stimulation (Ghosh, 1998, Annu. Rev. Immunol., 16, 225-260; Karin, 1999, J. Biol. Chem., 274, 27339-27342; Israel, 2000, Trends Cell. Biol., 10, 129-133; Santoro, 2003, EMBO J., 22, 2552-2560). In mammalian cells, there are five NFκB family members that dimerize: RelA, RelB, c-Rel, NFκB 2/p100/p52 and NFκB 1/p105/p50. NFκB, whose predominant form is a heterodimeric transcription factor composed of p50 and RelA subunits, remains sequestered in the cytoplasm through association with members of an inhibitory family of proteins known as IκB. Upon stimulation by the cytokines TNF-α and interleukin-1, endotoxin (LPS), microbial and viral infections, pro-inflammatory signals converge on the canonical IkB kinase complex (IKK), a protein complex that is composed of two kinase subunits, IKKα/IKK-1 and IKKβ/IKK-2 and a structural/regulatory subunit NEMO/IKK-γ. Once activated IKK complex phosphorylates IkB proteins, triggering their ubiquitination and subsequent degradation by the proteasome. Free NFκB can then move into nucleus to initiate or up-regulate gene expression.

Although IKKα and IKKβ exhibit striking structural similarity (52%), genetic studies have shown that they are involved in two pathways for the activation of NFκB (Pomerantz, 2002, Molecular Cell 2002 10: 693-695). IKKβ has been identified as the pro-inflammatory kinase responsible of activation of classical NFκB complexes, whereas IKKα in association with NFκB inducing kinase (NIK) plays an essential role in the non-canonical NFκB signaling pathway (Senftleben, 2001, 293: 1495-1499).

NFκB plays an essential role in the development and progression of cancer, including breast cancer. Animal studies suggest the presence of constitutively active NFκB at an early stage during neoplastic transformation of mammary cells (Clarkson et al., 2000, J Bio Chem. 275(17):12737-42). NFκB inhibits apoptosis in mouse mammary epithelia (Sovak et al., 1999, Cell Growth Differ. 10(8):537-44) and selective activation of NFκB subunits have been found in human breast cancer cell lines and patient samples (Sovak et al., 1997, J Clin Invest. 100(12):2952-60; Cogswell et al., 2000, Oncogene 19(9):1123-31). An inverse correlation between the levels of NFκB activation and estrogen receptor expression has been reported (Nakshatri et al., 1997, Mol Cell Biol. 17(7): 3629-39) and inhibition of NFκB in breast cancer cells induces spontaneous apoptosis (Sovak et al., 1999, Cell Growth Differ. 10(8):537-44; Cogswell et al., 2000, Oncogene 19(9):1123-31). Paclitaxel-induced sensitivity of breast cancer cell lines was enhanced by an NFκB inhibitor, parthenolide (Patel et al., 2000, Oncogene 19(36):4159-69; Newton et al., 1999, J Bio Chem. 274(26):18827-35). The Mullerian inhibiting substance was also found to inhibit breast cancer growth through NFκB mediated pathway (Segev et al., 2000, J Bio Chem. 275(37):28371-9). Furthermore, the transactivation function of NFκB is negatively regulated by IκBβ1 in breast cancer cell lines (Newton et al., 1999, J Bio Chem. 274(26):18827-35). Lastly, overexpression of HER2/neu can activate NFκB through the activation of Akt pathway and block apoptosis (Zhou et al., 2000, J Bio Chem. 275(10):8027-31). All these reports together suggest that NFκB plays an important role in cancer generally and in breast cancer specifically.

In light of the foregoing, inhibition of NFκB activation represents a target for development of new anti-inflammatory and anti-cancer drugs (Poulaki, 2002, Am J Pathol. 161: 2229-2240). Among many protein actors in NFκB signaling pathway, IKK complex represents one of the most promising molecular targets for discoveries of new specific NFκB inhibitors. To minimize the potential toxicity effects in vivo, therapeutic success will greatly depend on the abilities of the NFκB inhibitors to block activating signals without modifying the basal level of NFκB activity. For example, May et al. described a cell-permeable peptidic inhibitor that specifically blocks the pro-inflammatory NFκB activation by disrupting the constitutive NEMO interaction with IKK kinases (May, 2000, Science 289, 1550-1554; May, 2002, J. Biol. Chem. 277, 45992-46000). Accordingly, it would be desirable to identify additional small molecules that can reduce NFκB activity by selectively inhibiting NFκB and/or components of the NFκB signaling pathway.

3. SUMMARY OF THE INVENTION

The present invention relates to compounds which inhibit NFκB activity. The compounds of the invention may be used to inhibit NFκB activity in a subject, or in a cell in culture.

The present invention also provides a method for the treatment of a dysfunction of cell proliferation, the immune system and/or inflammation in an individual, wherein the dysfunction is associated with NFκB activity, by administering to an individual in need of such treatment a pharmaceutical composition comprising at least one compound of Formulas I-III in an amount effective to treat the dysfunction.

In particular non-limiting embodiments, the present invention relates to a compound of Formula I:

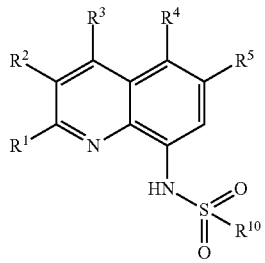

and to salts, esters and prodrugs of the compounds of Formula I. Additionally, the present invention describes methods of synthesizing and using compounds of Formula I.

In other non-limiting embodiments, the present invention relates to a compound of Formula II:

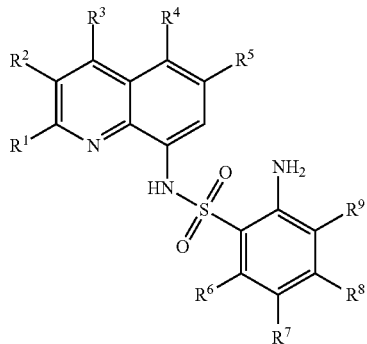

and to salts, esters and prodrugs of the compounds of Formula II. Additionally, the present invention describes methods of synthesizing and using compounds of Formula II.

In further non-limiting embodiments, the present invention relates to a compound of Formula III:

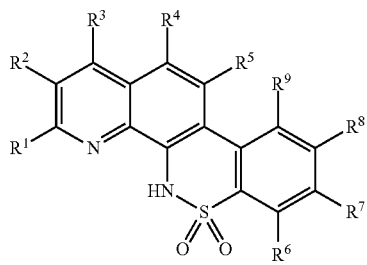

and to salts, esters and prodrugs of the compounds of Formula III. Additionally, the present invention describes methods of synthesizing and using compounds of Formula III.

The present invention also provides a method of inhibiting the activity of NFκB, by contacting the NFκB, an NFκB associated protein, or a cell expressing NFκB, with at least one compound of Formulas I-III (meaning Formula I, Formula II, or Formula III) in an amount effective to inhibit the activity of NFκB.

In one non-limiting embodiment, the NFκB is expressed by a cell, for example, a mammalian cell, and the cell is contacted with an effective amount of at least one compound of Formulas I-III.

In another embodiment, the NFκB, or cell expressing NFκB, is contacted with an effective amount of at least one compound of Formulas I-III in vitro.

In other non-limiting embodiments, the pharmaceutical composition may optionally be used in conjunction with one or more additional compound for the treatment of a dysfunction of cell proliferation, the immune system and/or inflammation.

It has further been discovered that some of these compounds inhibit BACE1, an enzyme that participates in the production of Aβ. As Aβ has been linked to neurodegeneration and to Alzheimer's Disease in particular, such compounds may be used in the treatment of neurodegenerative conditions and in particular in Alzheimer's Disease and related conditions.

4. BRIEF DESCRIPTION OF THE DRAWINGS

Figure 3A:
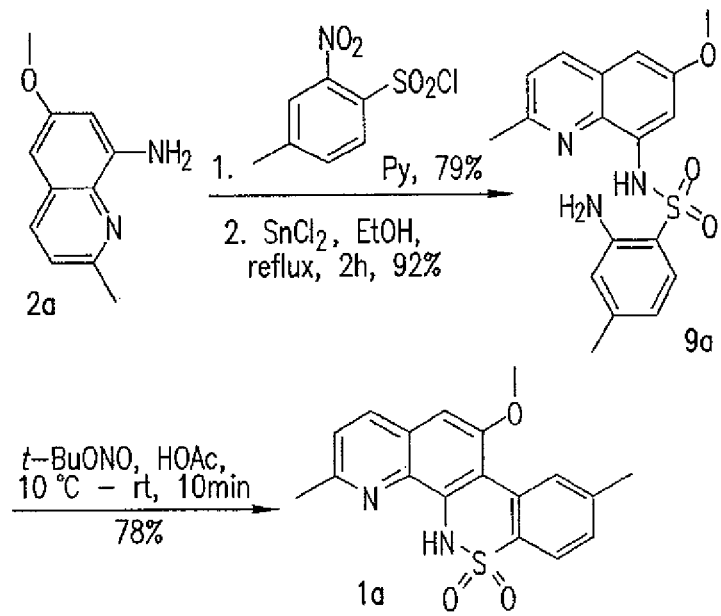
Figure 3B:
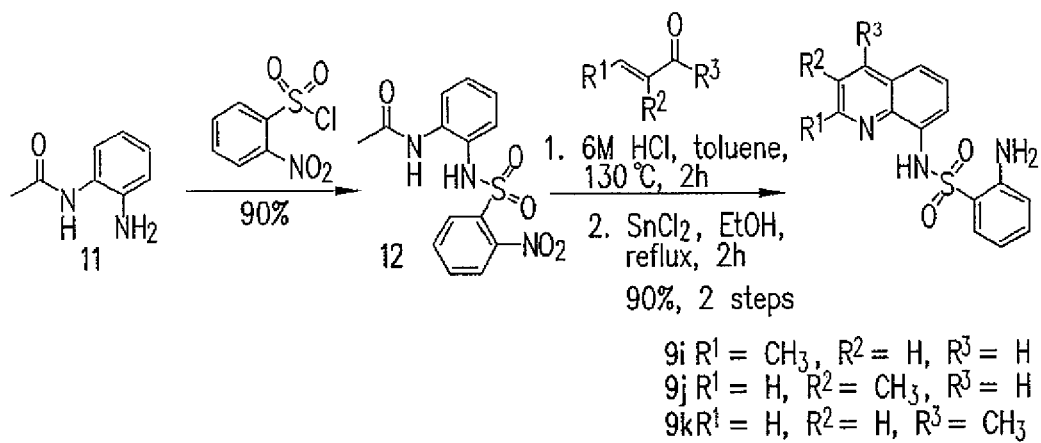

FIG. 3A-B depicts (A) a one-pot synthesis reaction mechanism synthesizing compound 9a of Formula II and compound 1a of Formula III. (B) depicts the synthesis of particular compounds of Formula II (the particular compounds identified as 9i, 9j, and 9k).

Figure 4:
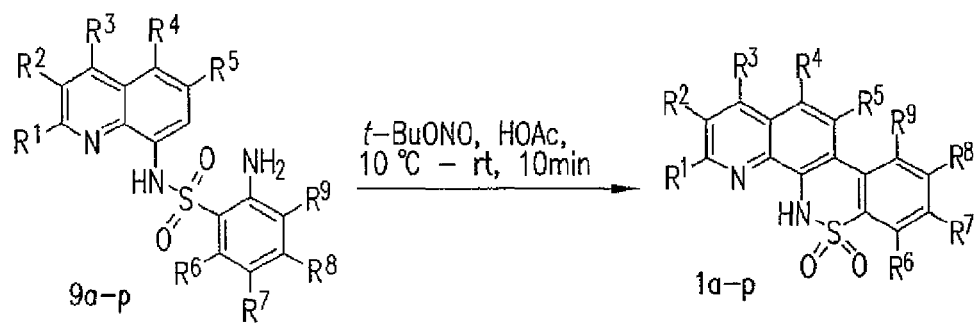

FIG. 4 depicts a one-pot synthesis reaction mechanism for converting particular compounds of Formula II into particular compounds of Formula III. The particular R groups of the starting compounds (9a-p) and the corresponding synthesized compounds (1a-p) are identical in each synthesis, and are illustrated in the table along with the individual yields of compounds 1a-p.

Figure 5A:
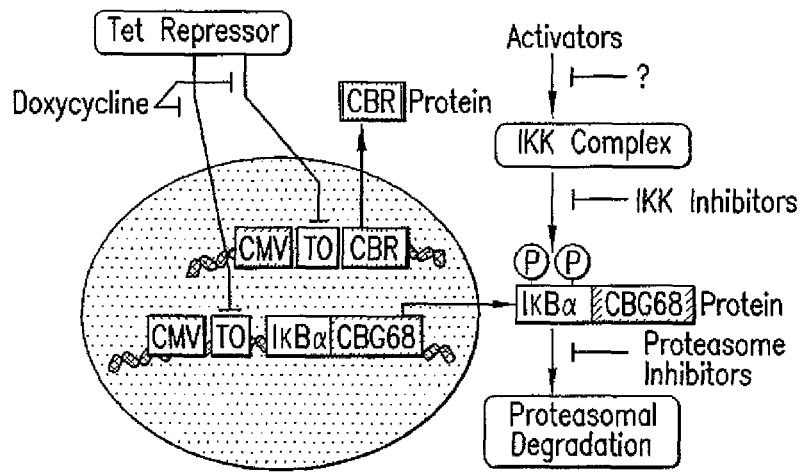
Figure 5B:
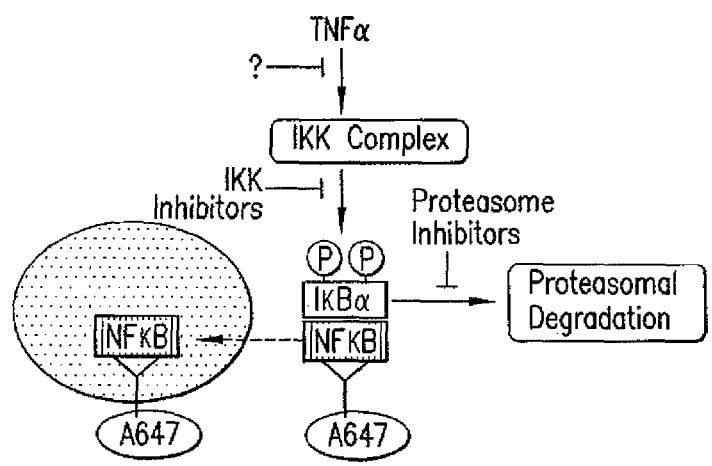

FIG. 5A-B depicts (A) The two-color dual luciferase based assay. IκBα is fused to a luciferase emitting greenlight (CBG68), while a red light-emitting luciferase (CBR) is present in its native state. Both luciferases are regulated by binding of the tet repressor to the tet operator (TO) binding site (TO), allowing simultaneous induction of the luciferases by the CMV promoter upon addition of doxycycline and test compounds. The CBR protein serves to normalize for non-specific effects, while the levels of the IκBα-CBG68 protein increase uniquely with inhibition of the NFκB pathway leading to IκBα degradation. (B) The nuclear translocation assay. TNFα stimulation results in nuclear translocation of NFκB, which is detected by immunofluorescence using an anti-p65 antibody and a secondary antibody labeled with an Alexa 647 fluorophore (A647).

Figure 6:
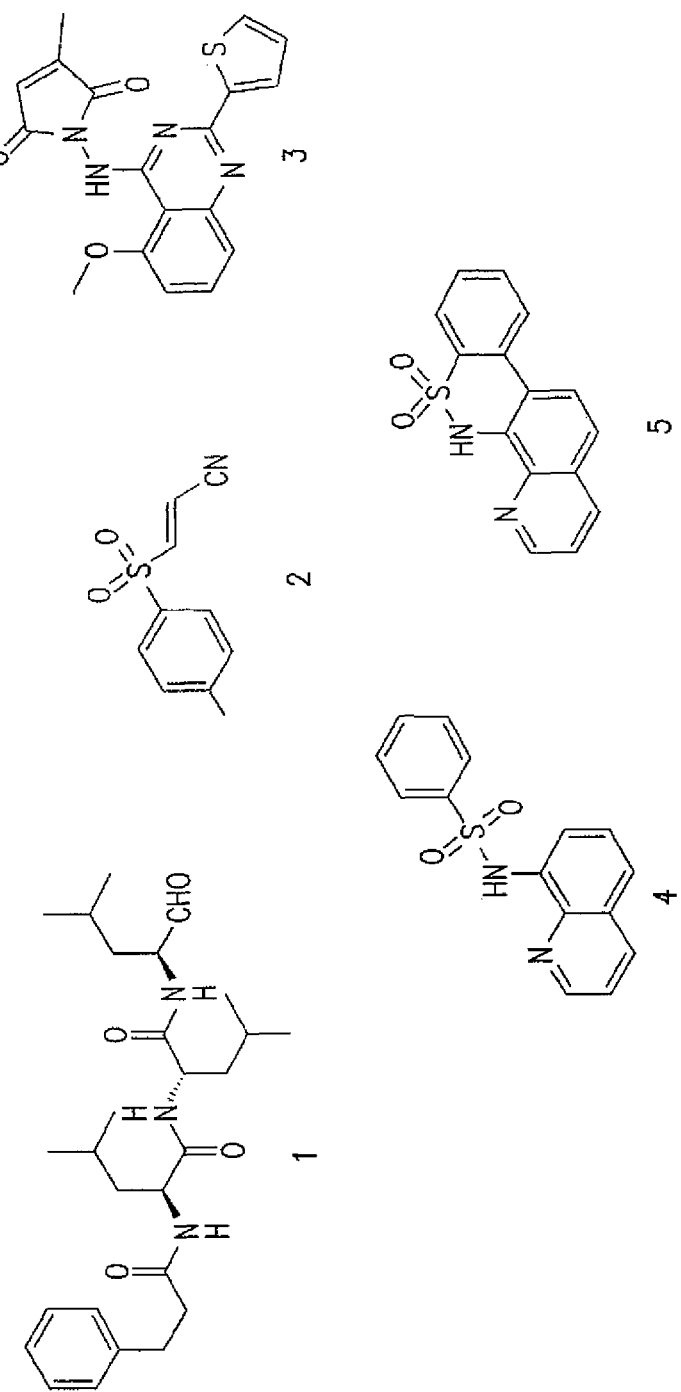

FIG. 6 depicts several compounds identified by the NFkB inhibition screens illustrated in FIG. 4, including Structures of MG-132 (1), BAY11-7082 (2), a quinazoline based inhibitor of Aβ$_1$ and NFκB mediated transcription (3), N-(quinolin-8-yl)benzenesulfonamide; PubChem CID: 161167 (4), and C7-locked N-(quinolin-8-yl)benzenesulfonamide (5); PubChem CID: 659101.

Figure 7D:
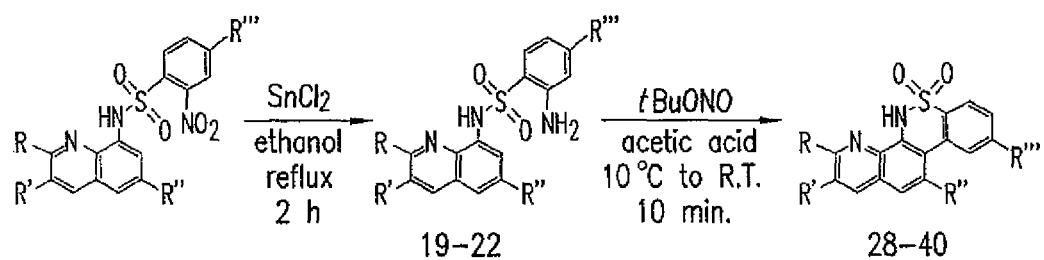

FIG. 7A-D depicts the NFκB inhibitory effect achieved by exemplary compounds of Formulas I and III in three cell-based NFκB activity assays. FIGS. 7A and C show the inhibitory effect of the compounds as measured by an IκBα stabilization assay, NFκB nuclear-translocation assay, and NFκB-bla expression assay. In the IκBα stabilization assay, a higher efficacy of IκBα stabilization compared to stabilization achieved by MG-132 (an IκBα stabilizing agent) indicates greater NFκB inhibition. IκBα stabilization was measured as an increase in luminescence of a green luciferase IκBα construct. Stabilization at a lower $EC_{50}$ concentration further indicates more potent NFκB inhibition. A red luciferase under the same regulatory control as the IκBα construct was used as a control to monitor cell uniformity and non-specific effects. Compounds that stabilized IκBα were those that increased green luminescence with minimal effects on red luminescence. In the nuclear-translocation and NFκB-bla expression assays, inhibition of NFκB nuclear-translocation or NFκB-bla expression at a lower $IC_{50}$ concentration indicates a stronger NFκB inhibitory effect. Cytotoxicity for each compound is also shown. FIG. 7B shows the synthetic scheme used to generate compounds 6-18 and 23-28 of Formula I. FIG. 7D shows the synthetic scheme used to generate compounds 19-22 of Formula I and compounds 28-40 of Formula III.

FIG. 8 depicts a sAPPβ assay utilized to identify inhibitors of BACE1. The assay utilizes SY5Y cells stably overexpressing BACE-GFP and SEAP-APPwt. Cells are incubated with a candidate compound for 6 hours prior to harvesting media. BACE1-mediated cleavage of APP results in the release of sAPPβ into the media. α-secretase, a competing enzyme that is non-amyloidogenic, also cleaves APP to release sAPPβ. Using an sAPPβ-specific antibody (sβwt), SEAP-sAPPβ is specifically captured in a modified ELISA assay. Detection is achieved by addition of the fluorescent alkaline phosphatase substrate, 4-methylumbelliferyl phosphate (4-MUP).

FIG. 9A-B depicts a targeted screen of N-(quinolin-8-yl)benzenesulfonamides, a small-scale screen using 176 structurally-related compounds based on the scaffold of N-(quinolin-8-yl)benzenesulfonamides. A) Primary screen was conducted in 96-well format at 2 µM concentration in duplicate. Data points represent mean of two determinations. The Z' factors for the four 96-well plates used in the screen were all above 0.7. B) Statistics from the primary screen. The threshold value for hit selection was set at 3 standard deviations, or 59.76%, yielding 6 hit compounds and a hit rate of 3.41%.

FIG. 10A-B depicts SAR studies of N-(quinolin-8-yl)benzenesulfonamides. 28 full and partial hits, shown in (A) for compounds 1-26 and (B) for compounds 27 and 28, from the targeted screen of N-(quinolin-8-yl)benzenesulfonamides were characterized in SY5Y-BACEGFP-SEAPAPPwt cells using the cell-based BACE1 assay. All compounds were tested at 8 concentrations (30, 10, 3, 1, 0.3, 0.1, 0.03, and 0.01 µM), and data points were analyzed with Origin software and fitted using a logistic model for $IC_{50}$ determination.

FIG. 11A-B depicts Lentiviral-mediated transduction of APPsw in primary neurons. Primary cortical neurons were harvested from wild-type P0 mice and cultured according to established protocols. Lentivirus harboring human Swedish mutant APP (Lenti-APPsw) was packaged using ViraPower Lentiviral Packaging mix (Invitrogen) according to the manufacturer's protocol. DIV-14 neurons were incubated for 24 hours with primary culture media containing the indicated volume (in µl) of virus (LV-1 and LV-2 denote 2 separate batches of virus, 0 denotes no virus was used). After infection, neurons were incubated for 72 hours with primary culture media. Media was collected for Aβ40 ELISA (Bio Source), and cell lysates were probed with APPCT antibody to visualize transduced full-length APP. (A) Bar graph depicting results; (B) Assay results.

Figure 12:
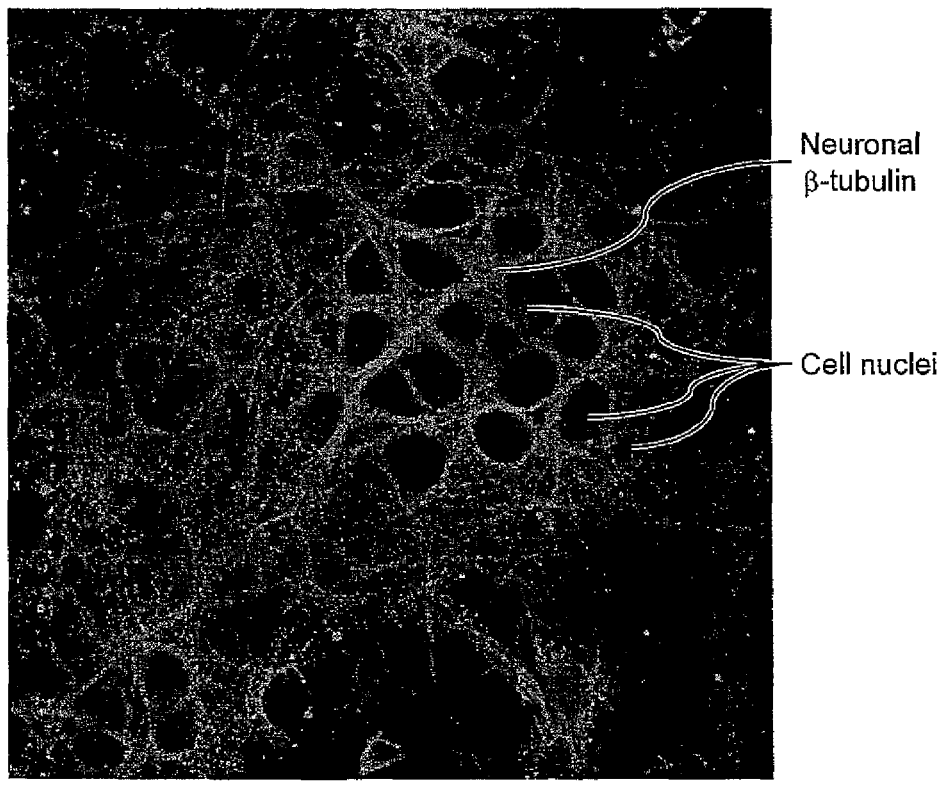

FIG. 12 depicts immunocytochemistry of primary cortical neurons. DIV-14 primary cortical neurons from wild-type mice were fixed, permeabilized, and stained with TUJ1 to visualize neuronal β-tubulin (green). Cell nuclei (blue) were visualized with a DAPI co-stain. Cells were imaged with the Nikon C1 digital confocal system at 60× magnification.

Figure 13A:
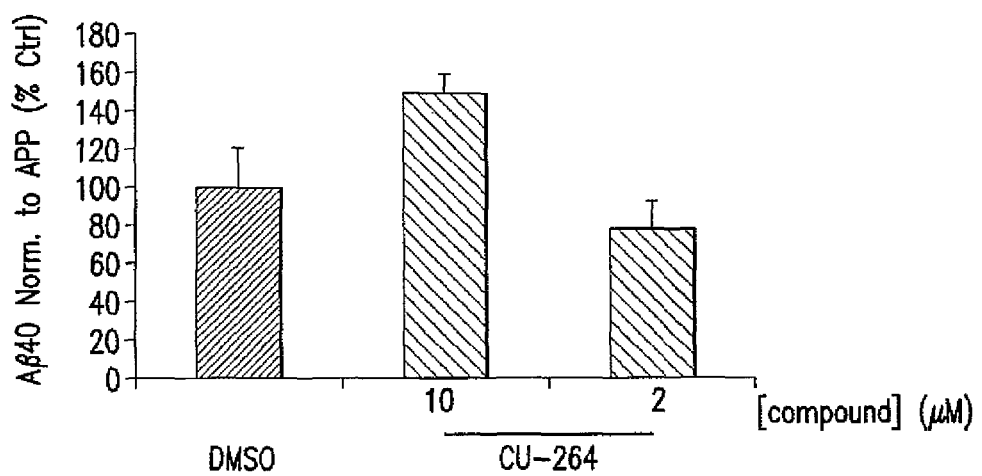
Figure 13B:
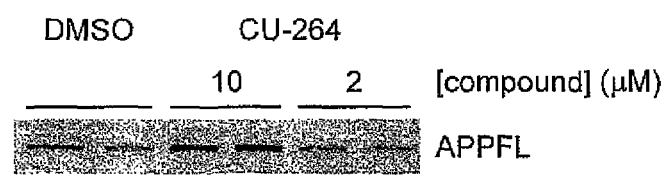

FIG. 13A-B depicts the effect of CU-264 on Aβ expressing primary cortical neuron cultures from wild-type mice transformed with lentivirus harboring APPsw. CU-264, which exhibited sub-micromolar potency for sAPPβ reduction in SY5Y-BACEGFP-SEAPAPPwt cells, does not reduce $Aβ_{40}$ levels in primary neurons when the cells are incubated with 2 µM CU-264. At 10 µm, CU-264 increased Aβ levels. (A) Bar graph depicting results; (B) Assay results.

5. DETAILED DESCRIPTION

For clarity and not by way of limitation, this detailed description is divided into the following sub-portions:
(i) definitions;
(ii) synthesis schemes;
(iii) methods of treatment; and
(iv) pharmaceutical compositions.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

In one non-limiting embodiment, the NFκB is a human NFκB. The NFκB is preferably, but not by way of limitation, encoded by the *Homo sapiens* nuclear factor of kappa light polypeptide gene enhancer in B-cells 1 (NFKB1) (GenBank accession number NM_003998), *Homo sapiens* nuclear factor of kappa light polypeptide gene enhancer in B-cells 2 (p49/p100) (NFKB2) (GenBank accession numbers NM_001077493, NM_001077494, or NM_002502), *Homo sapiens* v-rel reticuloendotheliosis viral oncogene homolog A (avian) (RELA) (GenBank accession number NM_021975), *Homo sapiens* v-rel reticuloendotheliosis viral oncogene homolog B (RELB) (GenBank accession number NM_006509), or *Homo sapiens* v-rel reticuloendotheliosis viral oncogene homolog (avian) (REL) (GenBank accession number NM_002908), or any nucleic acid that encodes a human NFκB polypeptide. Alternatively, NFκB can be encoded by any nucleic acid molecule exhibiting at least 50%, at least 60%, at least 70%, at least 80%, at least 90%, at least 95%, or up to 100% homology to any one of the NFκB genes (as determined by standard software, e.g. BLAST or FASTA), and any sequences which hybridize under stringent conditions to these sequences, which retain NFκB activity.

In other non-limiting embodiments, an NFκB of the invention may be characterized as having an amino acid sequence described by GenBank accession numbers: NP_003989, NP_001070961, NP_001070962, NP_002493, NP_068810, NP_006500, and NP_002899, or any other amino acid sequence at least 90% homologous thereto which retains NFκB activity.

In another embodiment, NFκB comprises a family of proteins which includes, but is not limited to, the proteins NFκB1 (p50), NFκB2 (p52), RelA (p65), RelB and c-Rel.

The BACE1, NFκB or APP may be a recombinant BACE1, NFκB or APP polypeptide encoded by a recombinant nucleic acid, for example, a recombinant DNA molecule, or may be of natural origin.

The term "dysfunction of the immune system" refers to any irregular activation of the innate and adaptive immune response associated with an increase in NFκB activity, for example, aberrant T-cell or B-cell development, maturation, and/or proliferation.

The term "inflammation" encompasses both acute responses (i.e., responses in which the inflammatory processes are active) as well as chronic responses (i.e., responses marked by slow progression and formation of new connective tissue). In certain non-limiting embodiments, a disease associated with inflammation that is to be treated by a compound of the instant invention is, by way of example, but not by way of limitation, type I hypersensitivity, atopy, anaphylaxis, asthma, osteoarthritis, rheumatoid arthritis, septic arthritis, gout, juvenile idiopathic arthritis, still's disease, ankylosing spondylitis, inflammatory bowel disease, Crohn's disease or inflammation associated with vertebral disc herniation.

According to the invention, a "subject" or "patient" is a human or non-human animal. Although the animal subject is preferably a human, the compounds and compositions of the invention have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

The term 'alkyl' refers to a straight or branched $C_1$-$C_{20}$, preferably $C_1$-$C_5$, hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl).

The term "alkenyl" refers to a $C_2$-$C_{20}$, preferably $C_1$-$C_5$, aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronaphthyl, adamantyl and norbornyl groups bridged cyclic group or spirobicyclic groups, e.g., Spiro (4,4) non-2-yl.

The term "aryl" refers to aromatic radicals having in the range of about 6 to about 14 carbon atoms such as phenyl, naphthyl, tetrahydronaphthyl, indanyl, biphenyl.

The term "heterocyclic" refers to a stable 3- to 15-membered ring radical which consists of carbon atoms and one or more, for example, from one to five, heteroatoms selected from the group consisting of nitrogen, oxygen and sulfur. For purposes of this invention, the heterocyclic ring radical may be a monocyclic or bicyclic ring system, which may include fused or bridged ring systems, and the nitrogen, carbon, oxygen or sulfur atoms in the heterocyclic ring radical may be optionally oxidized to various oxidation states. In addition, a nitrogen atom, where present, may be optionally quaternized; and the ring radical may be partially or fully saturated (i.e., heteroaromatic or heteroaryl aromatic).

The heterocyclic ring radical may be attached to the main structure at any heteroatom or carbon atom that results in the creation of a stable structure.

The term "heteroaryl" refers to a heterocyclic ring wherein the ring is aromatic.

The substituents in the 'substituted alkyl', 'substituted alkenyl', 'substituted cycloalkyl', 'substituted aryl,' 'substituted heteroaryl' 'substituted alkoxy,' 'substituted aryloxy,' 'substituted alkylthiol,' and 'substituted arylthiol' may be the same or different, with one or more selected from the groups hydrogen, halogen, acetyl, nitro, oxo (=O), $CF_3$, $NH_2$, $OCH_3$, or optionally substituted groups selected from alkyl, alkoxy and aryl.

The term "halogen" refers to radicals of fluorine, chlorine, bromine and iodine.

The term "BACE1" refers to a polypeptide which mediates the cleavage of APP in the β-amyloidgenic pathway, producing an sAPPβ ectodomain APP metabolite, which is released into the extracellular space, and an intracellular C-terminal fragment (CTF). In one non-limiting embodiment, the BACE1 is a human BACE1. The BACE1 is preferably encoded by the *Homo sapiens* beta-site APP-cleaving enzyme 1 (BACE1) gene (GenBank accession numbers NM_012104, NM_138972, NM_138971, or NM_138973), or any nucleic acid which encodes a human BACE1 polypeptide. Alternatively, BACE1 can be encoded by any nucleic acid molecule exhibiting at least 50%, at least 60%, at least 70%, at least 80%, at least 90%, at least 95%, or up to 100% homology to a BACE1 gene (as determined by standard software, e.g. BLAST or FASTA), and any sequences which hybridize under stringent conditions to these sequences which retain BACE1 activity, where stringent conditions are as described in U.S. Published Patent Application US20030082140, which is hereby incorporated by reference in its entirety and for all purposes.

In other non-limiting embodiments, a BACE1 of the invention may be characterized as having an amino acid sequence described by GenBank accession numbers: NP_036236, NP_620428, NP_620427 and NP_620429, or any other amino acid sequence at least 90%, or at least 95% homologous thereto, which retains BACE1 activity.

The terms "APP" or "amyloid precursor protein" refers to a substrate of BACE1 which may be metabolized into an ectodomain sAPPβ fragment and a C-terminal fragment (CTF). In one embodiment, APP is an integral membrane protein expressed in many tissues and concentrated in, for example, the synapses of neurons. In one non-limiting embodiment, APP is a human APP, for example, *Homo sapiens* amyloid beta (A4) precursor protein (APP) encoded by an APP gene (e.g., GenBank Accession numbers: NM_201414, NM_201413, or NM_000484), or any nucleic acid that encodes a human APP polypeptide. Alternatively, APP can be encoded by any nucleic acid molecule exhibiting at least 50%, at least 60%, at least 70%, at least 80%, at least 90%, at least 95%, or up to 100% homology to any one of the APP genes (as determined by standard software, e.g. BLAST or FASTA), and any sequences which hybridize under stringent conditions to these sequences.

In other non-limiting embodiments, APP may be characterized as comprising an amino acid sequence described by GenBank accession numbers: NP_958817, NP_958816, or NP_000475, or any other amino acid sequence at least 90% or at least 95% homologous thereto and is cleavable by a human BACE1 protein. In non-limiting embodiments APP may be comprised in a fusion protein.

5.2 Synthesis Schemes

The present invention provides for compounds that inhibit the activity of NFκB and/or BACE1.

In certain non-limiting embodiments, the invention provides for compounds of the following Formula I:

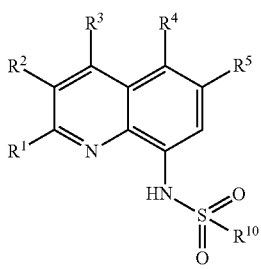

wherein $R^1$, $R^2$, $R^3$, $R^4$ and $R^5$ are independently selected for each occurrence from the group consisting of hydrogen, halogen, alkyl, aryl, alkoxy, aryloxy, alkylthiol, arylthiol, CN, and $NO_2$; and wherein $R^{10}$ is selected from the group consisting of substituted or unsubstituted alkyl, substituted or unsubstituted cycloalkyl, substituted or unsubstituted aryl, substituted or unsubstituted heteroaryl and substituted or unsubstituted alkenyl.

In non-limiting embodiments, $R^1$, $R^2$, $R^3$, $R^4$ and $R^5$ are independently selected for each occurrence from the group consisting of hydrogen, methyl, Cl, $OCH_3$, $CF_3$, Br, and F. In a specific non-limiting embodiment, $R^4$ and $R^5$ are hydrogen, and $R^1$, $R^2$, and $R^3$ are independently hydrogen, halogen, alkyl, aryl, CN, alkoxy, aryloxy, $NO_2$, alkylthio, and arylthio.

In other preferred embodiments, $R^{10}$ is selected from the group consisting of phenyl, naphthyl, 2-Nitrophenyl, 3-Nitrophenyl, 4-Nitrophenyl, 4-Methyl-2-nitrophenyl, 2-Methyl-5-nitrophenyl, 2-Nitro-4-(trifluoromethyl)phenyl, 4-Methoxy-2-nitrophenyl, 2-Methyl-5-nitrophenyl, 4-Methyl-2-nitrophenyl, 4-Methylphenyl, 2-Aminophenyl, 2-Amino-4-methyl phenyl, Thiophen-2-yl, 5-Chlorothiophen-2-yl, 5-Bromothiophen-2-yl.

In one non-limiting embodiment, compounds of Formula I may be synthesized according to the following scheme:

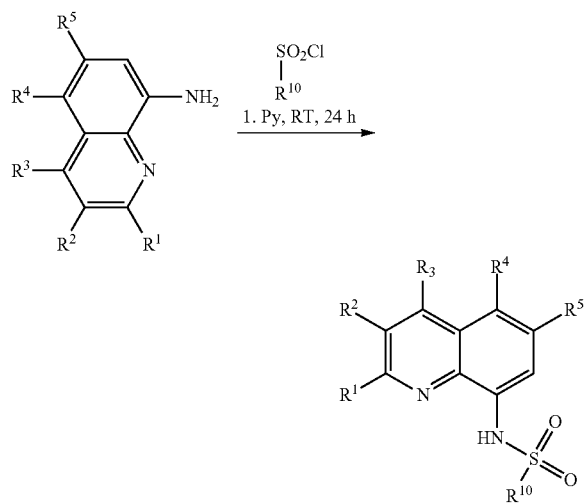

wherein $R^1$, $R^2$, $R^3$, $R^4$, $R^5$ and $R^{10}$ are defined as above for Formula I.

In other non-limiting embodiments, compounds of Formula I may be synthesized by any means known in the art.

In another non-limiting embodiment, the compound defined by Formula I is:

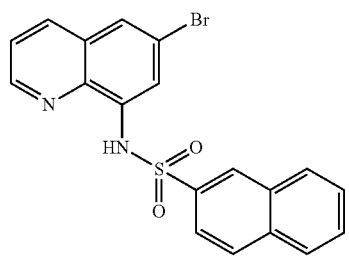 [SMILES: O=S(=O)(Nc1cc(Br)cc2cccnc12)c1ccc2ccccc2c1]

In other non-limiting embodiments, the compound defined by Formula I is:

A

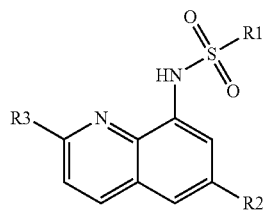

| Compound | R1 | R2 | R3 | IC$_{50}$ (sAPPβ) (μM) |
|---|---|---|---|---|
| CU-131 | 1-naphthalene | H | H | 6.46 |
| CU-138 | 1-naphthalene | Br | H | 9.51 |
| CU-150 | 2-thiophene | H | H | 8.03 |
| CU-151 | 4-methoxyphenyl | H | H | 5.92 |
| CU-152 | 4-nitrophenyl | H | H | 4.63 |
| CU-153 | 2-nitrophenyl | H | H | 1.58 |
| CU-155 | 2-naphthalene | H | H | 2.20 |
| CU-156 | 8-quinoline | H | H | 4.23 |
| CU-163 | 2-naphthalene | Br | H | 0.79 |
| CU-166 | phenyl | Br | H | 13.45 |
| CU-167 | 4-methylphenyl | Br | H | 1.09 |
| CU-168 | 8-quinoline | Br | H | 17.17 |
| CU-225 | 4-methylphenyl | H | Me | 3.79 |
| CU-242 | 2-aminophenyl | H | H | 3.82 |
| CU-261 | 4-methoxy-2-nitrophenyl | H | H | 1.92 |
| CU-264 | 4-trifluoromethyl-2-aminophenyl | H | H | 0.53 |
| CU-265 | 4-trifluoromethyl-2-nitrophenyl | H | H | 2.95 |
| CU-268 | 2-nitrophenyl | OMe | H | 8.11 |
| CU-271 | 4-methoxy-2-aminophenyl | H | H | 2.74 |
| CU-273 | 2-nitrophenyl | H | Me | 12.43 |
| CU-274 | 2-aminophenyl | H | Me | 11.11 |
| CU-278 | 4-methoxy-2-aminophenyl | H | Me | 11.48 |
| CU-280 | 4-trifluoromethyl-2-nitrophenyl | H | Me | 5.51 |
| CU-281 | 4-trifluoromethyl-2-aminophenyl | H | Me | 3.28 |
| CU-294 | 2-naphthalene | OMe | H | 3.75 |
| CU-295 | 1-naphthalene | OMe | H | 3.63 |

B

| Compound | Structure | IC$_{50}$ (sAPPβ) (μM) |
|---|---|---|
| CU-262 | 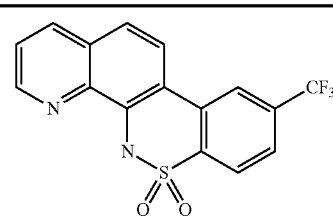 | 0.82 |

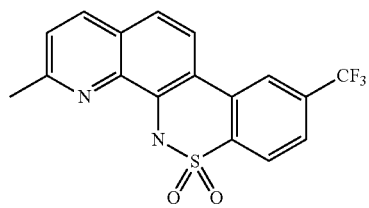 [SMILES: Cc1ccc2ccc3c(c2n1)NS(=O)(=O)c1ccc(C(F)(F)F)cc1-3]

CU-282                1.11

In other non-limiting embodiments, the invention provides for compounds of the following Formula II:

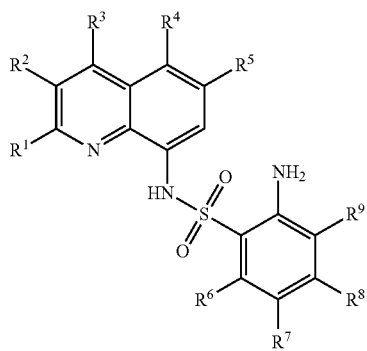

wherein $R^1$, $R^2$, $R^3$, $R^4$, $R^5$, $R^6$, $R^7$, $R^8$ and $R^9$ are independently selected for each occurrence from the group consisting of hydrogen, halogen, substituted or unsubstituted alkyl, substituted or unsubstituted aryl, substituted or unsubstituted alkoxy, substituted or unsubstituted aryloxy, substituted or unsubstituted alkylthiol, substituted or unsubstituted arylthiol, CN, and $NO_2$. In a specific non-limiting embodiment, $R^4$ and $R^5$ are hydrogen, and $R^1$, $R^2$, and $R^3$ are independently hydrogen, halogen, alkyl, aryl, CN, alkoxy, aryloxy, $NO_2$, alkylthio, and arylthio.

In a non-limiting embodiment, $R^1$, $R^2$, $R^3$, $R^4$, $R^5$, $R^6$, $R^7$, $R^8$ and $R^9$ are independently selected for each occurrence from the group consisting of hydrogen, methyl, Cl, $OCH_3$, $CF_3$ and F.

In another non-limiting embodiment, the compound defined by Formula II is:

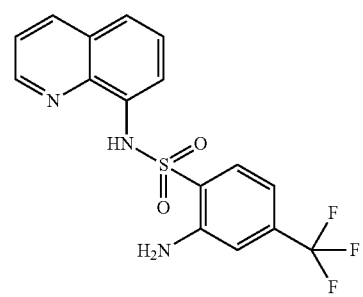 [SMILES: Nc1cc(C(F)(F)F)ccc1S(=O)(=O)Nc1cccc2cccnc12]

In another non-limiting embodiment, compounds of Formula II may be synthesized according to the following scheme:

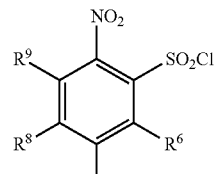

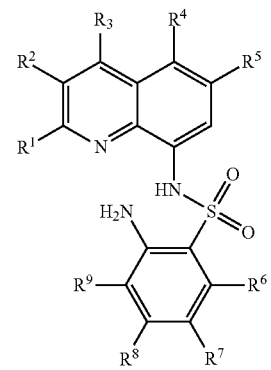

wherein $R^1$, $R^2$, $R^3$, $R^4$, $R^5$, $R^6$, $R^7$, $R^8$ and $R^9$ are defined as above for Formula II.

In other non-limiting embodiments, compounds of Formula II may be synthesized by any means known in the art.

In other non-limiting embodiments, the compounds of Formula II may be synthesized according to the following scheme:

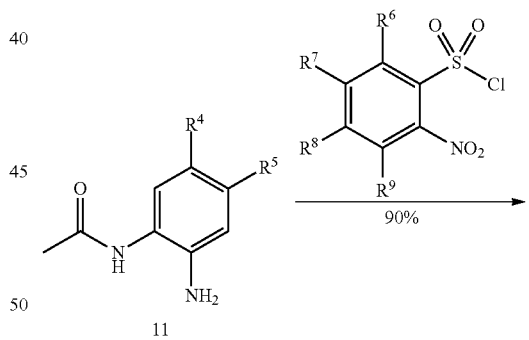

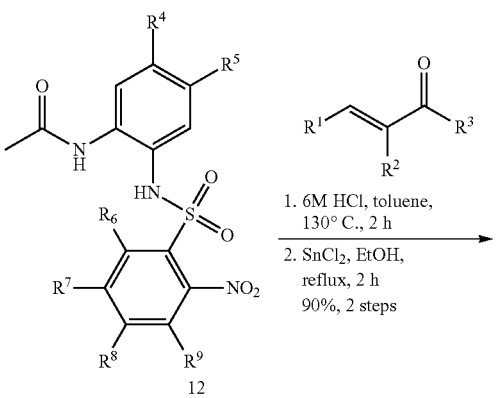

-continued

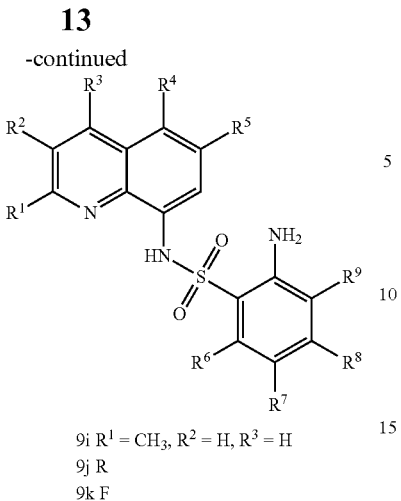

9i R¹ = CH₃, R² = H, R³ = H
9j R
9k F wherein R¹, R², R³, R⁴, R⁵, R⁶, R⁷, R⁸ and R⁹ are defined as above for Formula II.

In other non-limiting embodiments, the invention provides for compounds of the following Formula III:

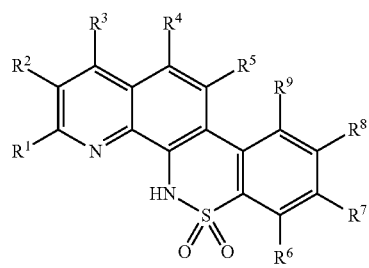

wherein R¹, R², R³, R⁴, R⁵, R⁶, R⁷, R⁸ and R⁹ are independently selected for each occurrence from the group consisting of hydrogen, halogen, alkyl, aryl, alkoxy, aryloxy, alkylthiol, arylthiol, CN, and NO₂.

In non-limiting embodiments, R¹, R², R³, R⁴, R⁵, R⁶, R⁷, R⁸ and R⁹ are independently selected for each occurrence from the group consisting of hydrogen, methyl, Cl, OCH₃, CF₃, OH, and F. In a specific non-limiting embodiment, R⁴ and R⁵ are hydrogen, and R¹, R², and R³ are independently hydrogen, halogen, alkyl, aryl, CN, alkoxy, aryloxy, NO₂, alkylthio, and arylthio.

In non-limiting embodiments, compounds of Formula III may be synthesized according to the following scheme:

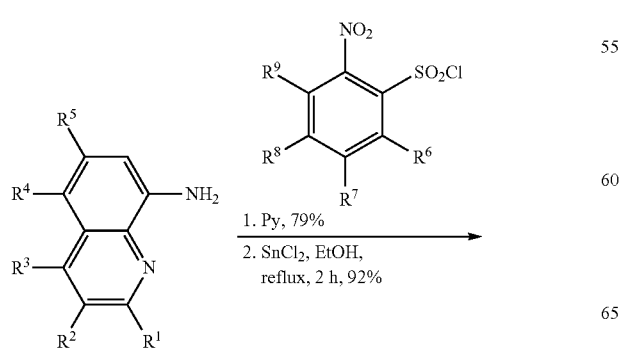

-continued

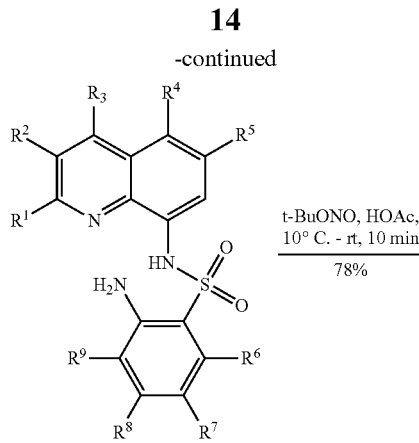

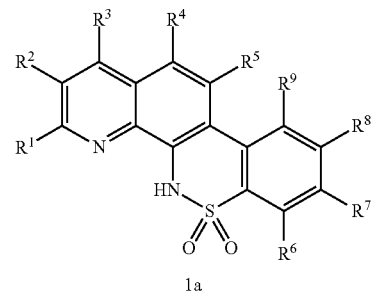

1a wherein R¹, R², R³, R⁴, R⁵, R⁶, R⁷, R⁸ and R⁹ are defined as above for Formula III.

In other non-limiting embodiments, compounds of Formula III may be synthesized by any means known in the art.

In other non-limiting embodiments, the compounds of Formula III may be synthesized according to the following scheme:

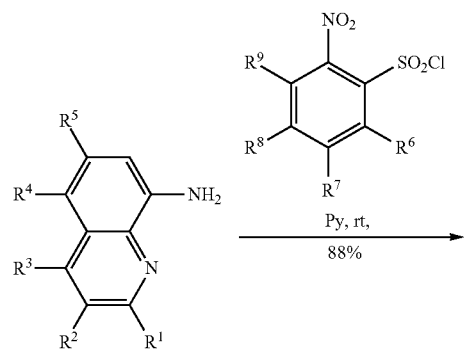

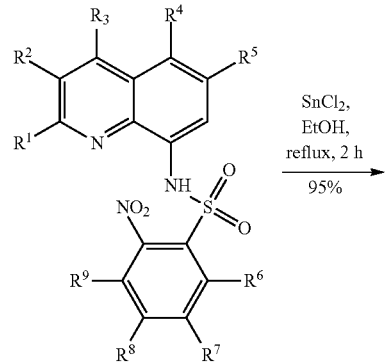

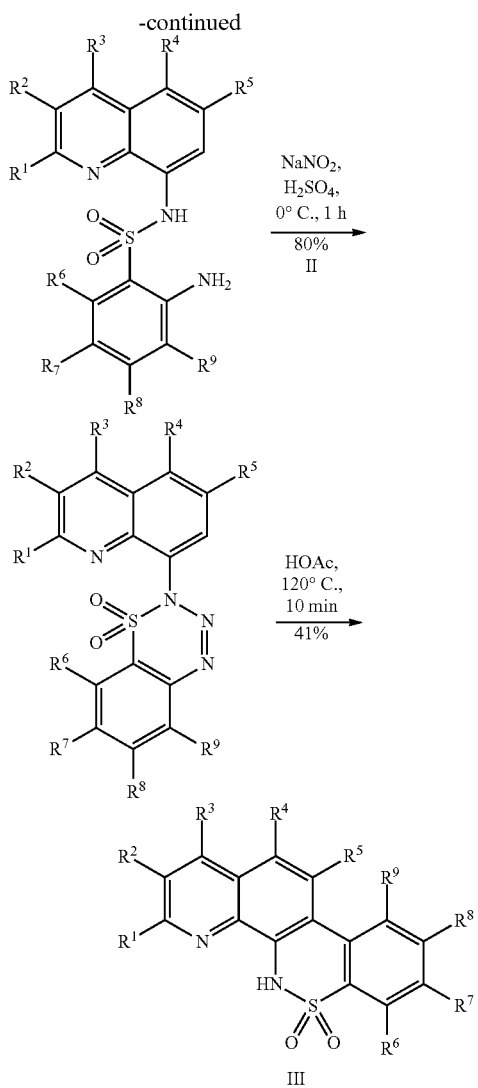

wherein $R^1$, $R^2$, $R^3$, $R^4$, $R^5$, $R^6$, $R^7$, $R^8$ and $R^9$ are defined as above for Formula III.

5.3 Methods of Treatment

In accordance with the invention, there are provided methods of using the compounds of Formulas I-III. The compounds of the instant disclosure can inhibit NFκB activity to exert beneficial effects. A compound of Formula I, II or III that inhibits NFκB activity may be used, in an effective amount, for the treatment of conditions including, but not limited to, cancer, tumorogenesis, and inflammatory conditions including, but not limited to, type I hypersensitivity, atopy, anaphylaxis, asthma, osteoarthritis, rheumatoid arthritis, septic arthritis, gout, juvenile idiopathic arthritis, still's disease, ankylosing spondylitis, inflammatory bowel disease, Crohn's disease or inflammation associated with vertebral disc herniation. A compound of Formula I, II or III that inhibits BACE1 activity may be used, in an effective amount, in the treatment of neurodegenerative diseases, such as Alzheimer's disease. In addition, the present invention is directed to the treatment of diseases related to dysfunction of cell proliferation, the immune system and/or inflammation.

5.3.1 Treatment Of Disease Related to Dysfunction of Cell Proliferation, the Immune System and/or Inflammation In non-limiting embodiments, the present invention provides for methods of treating diseases related to dysfunction of cell proliferation, the immune system and/or inflammation in a subject in need of such treatment by administration of a therapeutic formulation which comprises at least one compound of Formulas I-III.

In particular embodiments, the formulation may be administered to a subject in need of such treatment in an amount effective to inhibit NFkB activity. Where the formulation is to be administered to a subject in vivo, the formulation may be administered systemically (e.g. by intravenous injection, oral administration, inhalation, subcutaneous, intramuscular, etc.), intraventricularly, intrathecally, or by any other means known in the art. The amount of the formulation to be administered may be determined using methods known in the art, for example, by performing dose response studies in one or more model system, followed by approved clinical testing in humans.

In one embodiment, the subject or patient has been diagnosed with, or has been identified as having an increased risk of developing a disease associated with dysfunction of cell proliferation, the immune system and/or inflammation.

In other non-limiting embodiments, the present invention provides for methods of reducing in a subject, the risk of inflammatory damage comprising administering to the subject, an effective amount of a composition according to the invention. An effective amount may be a local concentration or, in a pharmaceutical composition, an amount that, when administered to a subject, results in a therapeutic benefit.

According to the invention, an effective amount is an amount of at least one compound of Formulas I-III which reduces one or more clinical symptom of one or more of the aforementioned diseases. In one example, an effective amount is an amount of at least one compound of Formulas I-III that reduces the activity of NFκB, for example, by stabilizing IκBα or by inhibiting nuclear translocation of NFκB.

In one non-limiting embodiment, the effective amount of at least one compound of Formulas may be determined, for example, via an in vitro assay wherein the effective amount of a compound of Formulas I-III may be correlated with the compound's ability to stabilize IκBα. By way of example, and not of limitation, such an assay may comprise a cell-based assay designed to identify compounds that stabilize IκBα, and thus reduce nuclear translocation of NFkB. The cell-based in vitro IkBα stabilization assay may utilize a dual reporter system, such as a luciferase reporter system in the cell line OCILy3, a model for primary tumors of the activated B-cell subtype (ABC) of diffuse large B-cell lymphoma (DL-BCL) (FIG. 5). The cell line used in the assay may exhibit a high NFκB activity level, for example, constitutive NFκB activity levels due to high levels of IKKβ activity leading to elevated expression of NFκB targeted genes. IKK and proteasome activity may produce high levels of IκBα degradation, liberating NFκB heterodimers to translocate to the nucleus.

According to the assay, modulators of IkBα stability may be identified by measuring changes in the level of expression of an IkBα reporter, for example, an exogenous IkBα-luciferase fusion reporter construct expressed by an NFkB-insensitive promoter. IkBα reporter expression may be measured in the presence or absence of a compound of the invention, wherein a greater increase in IkBα reporter expression by a cell contacted with the compound compared to the IkBα reporter expression in a cell not contacted with the compound is correlative with the therapeutic efficacy of the compound.

In one example, a dual luciferase IkBα stabilization screen in OCI-Ly3 may be used for high throughput screening (HTS). For example, but not by way of limitation, IkBα fused to a green light-emitting beetle luciferase and a red light-emitting beetle luciferase expressed in a native form can be used to monitor cell uniformity and non-specific effects. Fold-responsiveness may be further increased by having both reporters under the control of inducible promoters, for example, promoters regulated by doxycycline. Upon doxycycline induction of both luciferase reporters, compounds that increased green luminescence with minimal effects on the red luminescence signal may be identified as IkBα stabilizers, and thus an inhibitor of NFκB activity.

In one non-limiting embodiment, the cell based in vitro IkBα stabilization assay may be the assay depicted in FIG. 5a.

In one embodiment, an effective amount of a compound of Formulas I-III may be that amount which stabilizes IkBα, and a greater level of IkBα stabilization at a lower concentration when compared to a control level of IkBα stabilization, for example, as exhibited by a known IkBα stabilizing agent, such as MG-132 (FIG. 6) is correlative with the therapeutic efficacy of the compound.

In one embodiment, the compound may stabilize IkBα with an efficacy of at least about 10-20%, at least about 20-50%, at least about 50-100%, at least about 100-200%, at least about 200-400%, or at least about 400-800% when compared to the IkBα stabilization achieved by a known IkBα stabilizing agent, such as MG-132.

In one embodiment, an effective amount of a compound of Formulas I-III may be that amount which stabilizes IkBα with an $EC_{50}$ at a concentration ranging from about 200 μM to about 0.01 μM, preferably from about 100 μM to about 0.01 μM, more preferably from about 50 μM to about 0.01 μM, and more preferably from about 20 μM to about 0.01 μM in the in vitro assay, wherein an $EC_{50}$ at a lower concentration in the in vitro assay is correlative with the compound's therapeutic efficacy.

In another non-limiting embodiment, the effective amount of at least one compound of Formulas I-III may be determined, for example, via an in vitro assay wherein the effective amount of a compound of Formulas I-III may be correlated with the compound's ability to reduce the nuclear translocation of NFκB. By way of example, and not of limitation, such an assay may comprise a cell-based assay that utilizes an agent, for example, a cytokine such as TNFα, to stimulate nuclear translocation of endogenous NFκB. Stimulation by the agent may result in proteasome degradation of IkBα and subsequent translocation of NFkB from the cytoplasm to the nucleus, while in the absence of such a stimulatory agent, NFkB is sequestered in the cytoplasm due to its binding to IkBα.

In the nuclear-translocation in vitro assay, nuclear translocation of NFkB, for example, the endogenous p65 RelA subunit, may be detected and/or measured following stimulation with the agent through the use of, for example, but not limited to, fluorescent antibody detection and an automated imaging platform. Compounds of the invention may be contacted with cells of the in vitro assay, wherein a reduction in NFkB nuclear transport compared to a cell not contacted with the compound is indicative of the compound's ability to inhibit NFκB activity. According to the invention, a reduction in nuclear translocation of NFκB may be correlative with the compound's therapeutic efficacy.

In one non-limiting embodiment, the cell based nuclear-translocation in vitro assay may be the assay depicted in FIG. 5b.

In one embodiment, an effective amount of a compound of Formulas I-III may be correlated with the compound's ability to inhibit NFκB nuclear-translocation, wherein a greater level of inhibition at a lower concentration when compared to a control level of inhibition, for example, as exhibited by a known NFκB nuclear-translocation inhibitor, such as BAY 11-7082 (FIG. 6), is indicative of greater therapeutic efficacy of the compound.

In one embodiment, an effective amount of a compound of Formulas I-III may be that amount which inhibits NFκB nuclear-translocation with an efficacy of at least about 10-20%, at least about 20-50%, at least about 50-80%, or at least about 80-100% or more when compared to the NFκB nuclear-translocation inhibition achieved by a known inhibitor, such as BAY 11-7082.

In one non-limiting embodiment, an effective amount of a compound of Formulas I-III may be that amount which inhibits NFκB nuclear-translocation by at least 50% when the compound is administered at a concentration ranging from about 200 μM to about 0.01 μM, preferably from about 100 μM to about 0.01 μM, more preferably from about 50 μM to about 0.01 μM, and more preferably from about 10 μM to about 0.01 μM in the in vitro assay, wherein inhibition of NFκB nuclear-translocation at a lower concentration in the in vitro assay is correlative with the compound's therapeutic efficacy.

In another non-limiting embodiment, the effective amount of at least one compound of Formulas I-III may be determined, for example, via an in vitro assay wherein the effective amount of a compound of Formulas I-III may be correlated with the compound's ability to reduce expression of an NFκB-dependent reporter construct, for example, a β-lactamase reporter (NFκB-bla). By way of example, and not of limitation, such an assay may comprise contacting a cell expressing the NFκβ-dependent reporter construct, and monitoring the level of β-lactamase expression, wherein a decrease in expression compared to a cell not contacted with the compound indicates a reduction in NFκB activity. According to the invention, the reduction in expression of the NFκB-dependent reporter may be correlative with the compound's therapeutic efficacy.

In one non-limiting embodiment, an effective amount of a compound of Formulas I-III may be that amount which reduces expression of an NFκB-bla construct by at least 50% when the compound is administered at a concentration ranging from about 200 μM to about 0.01 μM, preferably from about 100 μM to about 0.01 μM, more preferably from about 50 μM to about 0.01 μM, and more preferably from about 10 μM to about 0.01 μM in the in vitro assay, wherein a reduction of NFκB-bla expression at a lower concentration in the in vitro assay is correlative with the compound's therapeutic efficacy.

In one non-limiting embodiment, an effective amount of a compound of Formulas I-III may be an amount which achieves a local concentration at the therapeutic site of about 100 μM to about 0.01 μM, preferably from about 50 μM to about 0.01 μM, more preferably from about 20 μM to about 0.01 μM, and more preferably from about 10 μM to about 0.01 μM in the in vitro assay.

5.3.2 Treatment of Neurodegenerative Diseases

The present invention provides for methods of treating a neurodegenerative disease in a subject in need of such treatment comprising administering, to the subject, a therapeutically effective amount of at least one compound of Formulas I-III. Non-limiting examples of neurodegenerative diseases include Alzheimer's disease, lewy body dementia, inclusion body myositis, and cerebral amyloid angiopathy.

In particular embodiments, the present invention provides for methods of treating diseases related to metabolism of APP by BACE1 in a subject in need of such treatment by administration of a therapeutic formulation which comprises an effective amount of at least one compound of Formulas I-III. In particular embodiments, the formulation may be administered to a subject in need of such treatment in an amount effective to inhibit BACE1 activity and/or reduce the presence of sAPPβ and/or Aβ. Where the formulation is to be administered to a subject in vivo, the formulation may be administered systemically (e.g. by intravenous injection, oral administration, inhalation, etc.), intraventricularly, intrathecally, or by any other means known in the art. The amount of the formulation to be administered may be determined using methods known in the art, for example, by performing dose response studies in one or more model system, followed by approved clinical testing in humans.

In one embodiment, the subject or patient has been diagnosed with, or has been identified as having an increased risk of developing a neurodegenerative disease, such as Alzheimer's Disease.

In other non-limiting embodiments, the present invention provides for methods of reducing in a subject, the risk of neural damage comprising administering, to the subject, an effective amount of a composition according to the invention. An effective amount may be a local concentration or, in a pharmaceutical composition, an amount that, when administered to a subject, results in a therapeutic benefit.

According to the invention, an effective amount is an amount of at least one compound of Formulas I-III which reduces one or more clinical symptom of one or more of the aforementioned diseases. In one example, an effective amount is an amount of at least one compound of Formulas I-III that reduces the production of sAPPβ or Aβ generated by the metabolism of APP by BACE1.

In one non-limiting embodiment, the effective amount of at least one compound of Formulas I-III may be determined via an in vitro assay, for example, as described in International Patent Application No. PCT/US2007/015938 (Publication No. WO 2008/008463), which is incorporated in its entirety herein for all purposes, wherein the effective amount may be correlated with the compound's ability to reduce the level of sAPPβ. By way of example, and not of limitation, such an assay may comprise a cell-based modified ELISA assay for measuring sAPPβ, the secreted ectodomain of β-amyloid precursor protein (APP) following β-secretase (BACE1) cleavage. Such an in vitro assay may be used to identify compounds of Formulas I-III that interfere with the first step of sAPPβ generation.

As described in the Examples below, and depicted in FIG. 8, the sAPPβ ELISA assay may comprise cells, for example, SY5Y cells, transfected with a BACE1 reporter construct, such as a GFP-tagged BACE1 (BACE-GFP), and a wild type APP reporter construct, such as a secreted alkaline phosphatase (SEAP)-tagged wild type APP (SEAP-APPwt). BACE1 cleavage of the reporter-tagged APP (e.g. SEAP-APPwt) may result in secretion into the media of SEAP-tagged sAPPβ, which may be collected and specifically captured using an sAPPβ cleavage site-specific antibody (e.g. sβwt). Following washing, a substrate may be used, for example, the fluorescent alkaline phosphatase substrate 4-methylumbelliferyl phosphate (4-MUP), to detect the captured SEAP-sAPPβ.

In one non-limiting example, an effective amount of a compound of Formulas I-III may be correlated with the compound's ability to reduce the level of sAPPβ detected in the in vitro assay compared to a control cell culture that was not contacted with the candidate compound, wherein a reduction of sAPPβ compared to the control cell culture correlates with the compound's therapeutic efficacy.

In another non-limiting example, an effective amount of a compound of Formulas I-III may be that amount which reduces the level of sAPPβ detected in the in vitro assay by at least 0.1, or by at least 0.5, or by at least 1, or by at least 1.5, or by at least 2, or by at least 2.5, or by at least 3, or by at least 3.5, or by at least 4, or by at least 4.5, or by at least 5, or by at least 5.5, or by at least 6 or more standard deviations above a control level of sAPPβ reduction detected in the in vitro assay when the compound is tested at a concentration of about 2 μM, or about 10 μM, wherein such a reduction of sAPPβ correlates with a compound's therapeutic efficacy. In one embodiment, the control level of sAPPβ reduction may be the average sAPPβ level in control cell cultures that are not contacted with the candidate compound. In other embodiments, the control level may be the average level of sAPPβ reduction achieved by a series of compounds tested in the in vitro assay.

In one preferred non-limiting embodiment, an effective amount of a compound of Formulas I-III may be correlated with the compound's ability to reduce sAPPβ levels by about 3 standard deviations greater than a control level of sAPPβ reduction when the compound is administered at a concentration of 2 μM in the in vitro assay.

In other preferred non-limiting embodiments; an effective amount of a compound of Formulas I-III may be correlated with the compound's ability to reduce the sAPPβ level by about 3 standard deviations greater than a control level of sAPPβ reduction when the compound is administered at a concentration of 10 μM in the in vitro assay.

In another example, an effective amount of a compound of Formulas may be that amount which reduces the level of sAPPβ by at least 5%, by at least 10%, by at least 20%, by at least 30%, by at least 40%, by at least 50%, by at least 60%, by at least 70%, by at least 80%, by at least 90%, or by 100% when compared to sAPPβ level in a control cell culture that was not contacted with the candidate compound, wherein such a reduction of sAPPβ correlates with a compound's therapeutic efficacy.

In another example, an effective amount of a compound of Formulas I-III may be that amount which reduces the level of sAPPβ by at least about 50% compared to a control cell culture that was not contacted with the candidate compound, wherein the compound is tested at a concentration ranging from about 200 μM to about 0.01 μM, preferably from about 100 μM to about 0.01 μM, and more preferably from about 10 μM to about 0.01 μM in the in vitro assay, wherein such a reduction of sAPPβ at the above-described concentrations is correlative with the compound's therapeutic efficacy.

In other preferred non-limiting embodiments, an effective amount of a compound of Formulas I-III may be correlated with the compound's ability to reduce the sAPPβ level by about at least 50% when the compound is administered at a concentration of about 0.5 μM in the in vitro assay.

In other preferred non-limiting embodiments, an effective amount of a compound of Formulas I-III may be correlated with the compound's ability to reduce the sAPPβ level by about at least 50% when the compound is administered at a concentration of about 1 µM in the in vitro assay.

In other preferred non-limiting embodiments, an effective amount of a compound of Formulas I-III may be correlated with the compound's ability to reduce the sAPPβ level by about at least 50% when the compound is administered at a concentration of about 2 µM in the in vitro assay.

In other preferred non-limiting embodiments, an effective amount of a compound of Formulas I-III may be correlated with the compound's ability to reduce the sAPPβ level by about at least 50% when the compound is administered at a concentration of less than 3 µM in the in vitro assay.

In other preferred non-limiting embodiments, an effective amount of a compound of Formulas I-III may be correlated with the compound's ability to reduce the sAPPβ level by about at least 50% when the compound is administered at a concentration of about 5 µM in the in vitro assay.

In other preferred non-limiting embodiments, an effective amount of a compound of Formulas I-III may be correlated with the compound's ability to reduce the sAPPβ level by about at least 50% when the compound is administered at a concentration of about 8 µM in the in vitro assay.

In other preferred non-limiting embodiments, an effective amount of a compound of Formulas I-III may be correlated with the compound's ability to reduce the sAPPβ level by about at least 50% when the compound is administered at a concentration of about 10 µM in the in vitro assay.

In other non-limiting embodiments, the effective amount of at least one compound of Formulas I-III may be correlated with the compound's ability to inhibit the enzymatic activity of a BACE1 enzyme. The compound's BACE1 inhibitory effect may be assayed, for example, through use of a BACE1 FRET Assay kit (Invitrogen Corp., Carlsbad, Calif., U.S.A.), wherein the fluorescence resonance energy transfer (FRET)-based assay measures the cleavage by purified recombinant β-secretase of a peptide substrate corresponding to the BACE1 cleavage site of Swedish mutant APP. In such an assay, a greater reduction in fluorescence in the reaction mixture following incubation with a compound of the invention compared to a control cell culture not contacted with the compound is correlative with the compound's therapeutic efficacy.

In one example, an effective amount of a compound of Formulas I-III may be that amount which inhibits BACE1 enzymatic activity by at least about 50% compared to a control cell culture that was not contacted with the candidate compound. Preferably the compound is tested at a concentration ranging from about 200 µM to about 0.01 µM, preferably from about 100 µM to about 0.01 µM, and more preferably from about 10 µM to about 0.01 µM in the in vitro assay, wherein such an inhibition of BACE1 enzymatic activity at the above-described concentrations is correlative with the compound's therapeutic efficacy.

In other non-limiting embodiments, the effective amount of at least one compound of Formulas I-III may be correlated with the compound's ability to reduce the level of Aβ$_{40}$ in an in vitro assay that measures the level of Aβ$_{40}$ produced in a cell line, for example, an SY5Y-BACEGFP-SEAPAPPwt cell line. In one non-limiting example, the level of Aβ$_{40}$ expressed by the cell line may be measured through the use of an Aβ$_{40}$ Elisa kit (BioSource). In one embodiment, the assay comprises incubating the Aβ$_{40}$ expressing cells with a compound of Formulas I-III, followed by assaying the concentration of Aβ$_{40}$ in the cell culture medium. In such an assay, a greater reduction of Aβ$_{40}$ concentration in the cell culture medium following incubation with a compound compared to a control cell culture not contacted with the compound is correlative with the compound's therapeutic efficacy.

In one example, an effective amount of a compound of Formulas I-III may be that amount which reduces the level of Aβ$_{40}$ in an in vitro assay by at least about 50% compared to a control cell culture that was not contacted with the candidate compound. Preferably the compound is tested at a concentration ranging from about 200 µM to about 0.01 µM, preferably from about 100 µM to about 0.01 µM, and more preferably from about 10 µM to about 0.01 µM in the in vitro assay, wherein such a reduction in the level of Aβ$_{40}$ at the above-described concentrations is correlative with the compound's therapeutic efficacy.

In other non-limiting embodiments, the effective amount of at least one compound of Formulas I-III may be correlated with the compound's ability to reduce the level of Aβ$_{40}$ in an in vitro assay that measures the level of Aβ$_{40}$ produced in a cell culture, for example, a culture of primary cortical neurons transduced with lentivirus carrying Swedish mutant APP (APPsw). In one embodiment, the assay comprises incubating the Aβ$_{40}$ expressing cells with a compound of Formulas I-III, followed by assaying the concentration of Aβ$_{40}$ in the cell culture medium. In such an assay, a greater reduction of Aβ$_{40}$ concentration in the cell culture medium following incubation with a compound compared to a control cell culture not contacted with the compound is correlative with the compound's therapeutic efficacy.

In one non-limiting embodiment, an effective amount of a compound of Formulas I-III may be that amount which reduces Aβ$_{40}$ by about 1-10%, more preferably from about 10-20%, more preferably from about 20-30%, more preferably from about 30-40%, more preferably from about 40-50%, more preferably from about 50-60%, more preferably from about 60-70%, more preferably from about 70-80%, more preferably from about 80-90%, and more preferably from about 90-100%, compared to Aβ$_{40}$ levels in the cell culture medium of a control cell culture that was not incubated with the compound. Preferably the compound is incubated at a concentration of about 200 µM to about 0.01 µM, preferably from about 100 µM to about 0.01 µM, and more preferably from about 10 µM to about 0.01 µM in the in vitro assay, wherein a greater level of Aβ$_{40}$ reduction at a lower concentration in the in vitro assay is correlative with the compound's therapeutic efficacy.

In other non-limiting embodiments, the effective amount of at least one compound of Formulas I-III may be correlated with the compound's ability to reduce the level of sAPPβ in an in vitro assay that measures the level of sAPPβ produced in a cell culture, for example, primary cortical neurons transduced with lentivirus carrying Swedish mutant APP (APPsw). In one embodiment, the assay comprises incubating the cells with a compound of Formulas I-III, followed by assaying the concentration of sAPPβ in the cell culture medium. In such an assay, a greater reduction of sAPPβ concentration in the cell culture medium following incubation with a compound compared to a control cell culture not contacted with the compound is correlative with the compound's therapeutic efficacy.

In one non-limiting embodiment, an effective amount of a compound of Formulas I-III may be that amount which reduces sAPPβ by about 1-10%, more preferably from about 10-20%, more preferably from about 20-30%, more preferably from about 30-40%, more preferably from about 40-50%, more preferably from about 50-60%, more preferably from about 60-70%, more preferably from about 70-80%, more preferably from about 80-90%, and more preferably from about 90-100%, compared to sAPPβ levels in the cell culture medium of a control cell culture that was not incubated with the compound. Preferably the compound is incubated at a concentration of about 200 µM to about 0.01 µM, preferably from about 100 µM to about 0.01 µM, and more preferably from about 10 µM to about 0.01 µM in the in vitro assay, wherein a greater level of sAPPβ reduction at a lower concentration in the in vitro assay is correlative with the compound's therapeutic efficacy.

In other non-limiting embodiments, an effective amount of a compound of Formulas I-III may be that amount which reduces $A\beta_{40}$ by about 50% in an in vitro assay compared to $A\beta_{40}$ levels in the cell culture medium of a control cell culture that was not incubated with the compound. Preferably the compound is incubated at a concentration of about 200 µM to about 0.01 µM, preferably from about 100 µM to about 0.01 µM, and more preferably from about 10 µM to 0.01 µM in the in vitro assay, wherein a reduction of $A\beta_{40}$ at a lower concentration in the in vitro assay is correlative with the compound's therapeutic efficacy.

In other non-limiting embodiments, the effective amount of at least one compound of Formulas I-III may be correlated with the compound's ability to reduce the level of $A\beta_{40}$ in an in vitro assay that measures the level of $A\beta_{40}$ produced in a cell culture, for example, cultured primary cortical neurons prepared from Tg2576 mice (i.e. mice carrying human APPsw transgene under the control of the PrP promoter). In one embodiment, the assay comprises incubating the $A\beta_{40}$ expressing cells with a compound of Formulas I-III, followed by assaying the concentration of $A\beta_{40}$ in the cell culture medium. In such an assay, a greater reduction of $A\beta_{40}$ concentration in the cell culture medium following incubation with a compound compared to a control cell culture not contacted with the compound is correlative with the compound's therapeutic efficacy.

In one non-limiting embodiment, an effective amount of a compound of Formulas I-III may be that amount which reduces $A\beta_{40}$ by about 1-10%, more preferably from about 10-20%, more preferably from about 20-30%, more preferably from about 30-40%, more preferably from about 40-50%, more preferably from about 50-60%, more preferably from about 60-70%, more preferably from about 70-80%, more preferably from about 80-90%, and more preferably from about 90-100%, compared to $A\beta_{40}$ levels in the cell culture medium of a control cell culture that was not incubated with the compound. Preferably when the compound is incubated at a concentration of about 200 µM to about 0.01 µM, preferably from about 100 µM to about 0.01 µM, and more preferably from about 10 µM to about 0.01 µM in the in vitro assay, wherein a greater level of $A\beta_{40}$ reduction at a lower concentration in the in vitro assay is correlative with the compound's therapeutic efficacy.

In other non-limiting embodiments, the effective amount of at least one compound of Formulas I-III may be correlated with the compound's ability to reduce the level of $A\beta_{40}$ and/or sAPPβ in an ex vivo assay that measures the level of $A\beta_{40}$ and/or sAPPβ produced in cells, for example, organotypic brain slices from Tg2576 mice (i.e. mice carrying human APPsw transgene under the control of the PrP promoter). In one embodiment, the assay comprises incubating the brain slices with a compound of Formulas I-III, followed by assaying the concentration of $A\beta_{40}$ and/or sAPPβ in the brain slices. In such an assay, a greater reduction of $A\beta_{40}$ and/or sAPPβ concentration in the brain slices following incubation with a compound compared to a control brain slice not contacted with the compound is correlative with the compound's therapeutic efficacy.

In one non-limiting embodiment, an effective amount of a compound of Formulas I-III may be that amount which reduces $A\beta_{40}$ and/or sAPPβ by about 1-10%, more preferably from about 10-20%, more preferably from about 20-30%, more preferably from about 30-40%, more preferably from about 40-50%, more preferably from about 50-60%, more preferably from about 60-70%, more preferably from about 70-80%, more preferably from about 80-90%, and more preferably from about 90-100%, compared to $A\beta_{40}$ and/or sAPPβ levels in control brain slices that were not incubated with the compound. Preferably the compound is incubated at a concentration of about 200 µM to about 0.01 µM, preferably from about 100 µM to about 0.01 µM, and more preferably from about 10 µM to about 0.01 µM in the ex vivo assay, wherein a greater level of $A\beta_{40}$ and/or sAPPβ reduction at a lower concentration in the ex vivo assay is correlative with the compound's therapeutic efficacy.

In other non-limiting embodiments, the effective amount of at least one compound of Formulas I-III may be correlated with the compound's ability to reduce the level of $A\beta_{40}$ and/or sAPPβ in an in vivo assay that measures the level of $A\beta_{40}$ and/or sAPPβ produced in a test subject, for example, a Tg2576 mouse (i.e. mice carrying human APPsw transgene under the control of the PrP promoter). In one embodiment, the assay comprises administering at least one compound of Formulas I-III to the test subject, for example, via interstitial fluid (ISF) compound administration, intraperitoneal (IP) compound injection, or through the use of a microdialysis apparatus for infusion of the compound at multiple concentrations (for example, in the hippocampus of the test subject), followed by assaying the concentration of $A\beta_{40}$ and/or sAPPβ in the test subject. In such an assay, a greater reduction of $A\beta_{40}$ and/or sAPPβ concentration in the test subject following administration of the compound compared to a control subject not administered the compound is correlative with the compound's therapeutic efficacy.

In one non-limiting embodiment, an effective amount of a compound of Formulas I-III may be that amount which reduces $A\beta_{40}$ and/or sAPPβ by about 1-10%, more preferably from about 10-20%, more preferably from about 20-30%, more preferably from about 30-40%, more preferably from about 40-50%, more preferably from about 50-60%, more preferably from about 60-70%, more preferably from about 70-80%, more preferably from about 80-90%, and more preferably from about 90-100%, compared to $A\beta_{40}$ and/or sAPPβ levels in brain homogenates of subjects that were not administered the compound. Preferably the compound is administered at a concentration of about 0.5 mg/kg to about 20 mg/kg, preferably from about 1 mg/kg to about 20 mg/kg, more preferably from about 3 mg/kg to about 20 mg/kg, more preferably from about 5 mg/kg to about 20 mg/kg, more preferably from about 10 mg/kg to about 20 mg/kg in the in vivo assay, wherein a greater level of $A\beta_{40}$ and/or sAPPβ reduction at a lower concentration in the in vivo assay is correlative with the compound's therapeutic efficacy.

In non-limiting embodiments, an effective amount of a compound of Formulas I-III may be an amount which achieves a local concentration at the therapeutic site of about 100 µM to about 0.01 µM, preferably from about 50 µM to about 0.01 µM, more preferably from about 20 µM to about 0.01 µM, and more preferably from about 10 µM to about 0.01 µM in the in vitro assay.

5.3.3 Administration of Treatments

According to the invention, the component or components of a pharmaceutical composition of the invention may be administered to a subject by means including but not limited to intravenous, intra-arterial, intramuscular, intradermal, transdermal, subcutaneous, oral, intraperitoneal, intraventricular, and intrathecal administration.

In particular non-limiting embodiments, the therapeutic compound can be delivered in a controlled or sustained release system. For example, a compound or composition may be administered using intravenous infusion, an implantable osmotic pump, a transdermal patch, liposomes, or other modes of administration. In one embodiment, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Langer and Wise eds., 1974, Medical Applications of Controlled Release, CRC Press: Boca Raton, Fla.; Smolen and Ball eds., 1984, Controlled Drug Bioavailability, Drug Product Design and Performance, Wiley, N.Y.; Ranger and Peppas, 1983, J. Macromol. Sci. Rev. Macromol. Chem., 23:61; Levy et al., 1985, Science 228:190; During et al., 1989, Ann. Neural., 25:351; Howard et al., 9189, J. Neurosurg. 71:105). In yet another embodiment, a controlled release system can be placed in proximity of the therapeutic target, i.e., the heart or a blood vessel, thus requiring only a fraction of the systemic dose (see, e.g., Goodson, 1984, in Medical Applications of Controlled Release, supra, Vol. 2, pp. 115-138). Other controlled release systems known in the art may also be used.

5.4 Pharmaceutical Compositions

The compounds and compositions of the invention may be formulated as pharmaceutical compositions by admixture with a pharmaceutically acceptable carrier or excipient.

For example, the pharmaceutical composition may comprise an effective amount of at least one compound of Formulas I-III and a physiologically acceptable diluent or carrier. The pharmaceutical composition may further comprise a second drug, for example, but not by way of limitation, an anticancer drug, an anti-inflammatory drug, for example, but not limited to, a steroid compound and/or a non-steroidal anti-inflammatory drug, or compound for the treatment of Alzheimer's disease, such as an acetylcholinesterase inhibitor or an NMDA glutamate receptor antagonist (e.g. memantine).

The phrase "pharmaceutically acceptable" indicates that a substance is physiologically tolerable when administered to a subject. Preferably, but not by way of limitation, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, or, for solid dosage forms, may be standard tabletting excipients. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

In a specific embodiment, the therapeutic compound can be delivered in a vesicle, in particular a liposome (see Langer, 1990, Science 249:1527-1533; Treat et al., 1989, in Liposomes in the Therapy of Infectious Disease and Cancer, Lopez-Berestein and Fidler eds., Liss: New York, pp. 353-365; Lopez-Berestein, ibid., pp. 317-327; see generally Lopez-Berestein, ibid.).

The present invention is not to be limited in scope by the specific embodiments described herein and the Examples that follow. Indeed, various modifications of the invention in addition to those described herein will become apparent to those skilled in the art from the foregoing description and the accompanying Examples and Figures. Such modifications are intended to fall within the scope of the appended claims.

Patents, patent applications, publications, product descriptions, GenBank Accession Numbers, and protocols are cited throughout this application, the disclosures of which are incorporated herein by reference in their entireties for all purpose.

EXAMPLES

Example 1

Synthesis of Compounds of Formulas I-III

The compounds of Formulas I and II consist of N-(quinolin-8-yl)benzenesulfonamides, and the compounds of Formula III consist of a structurally constrained cyclic sulfonamide with the sultam bridging quinolinyl and phenyl moieties. This particular scaffold lacks a general synthetic method. Described here is an efficient synthesis of this class of compounds that allows a diverse substitution pattern.

Figure 1A:
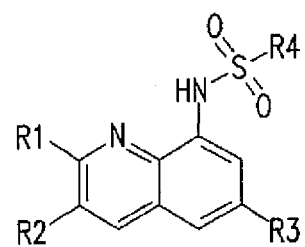
FIG. 1 depicts general structure of N-(quinolin-8-yl)benzenesulfonamides. A) Open chain and B) cyclized structures.
Figure 1B:
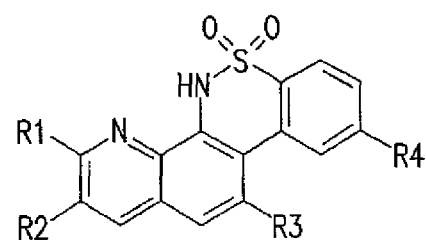
Figure 2:
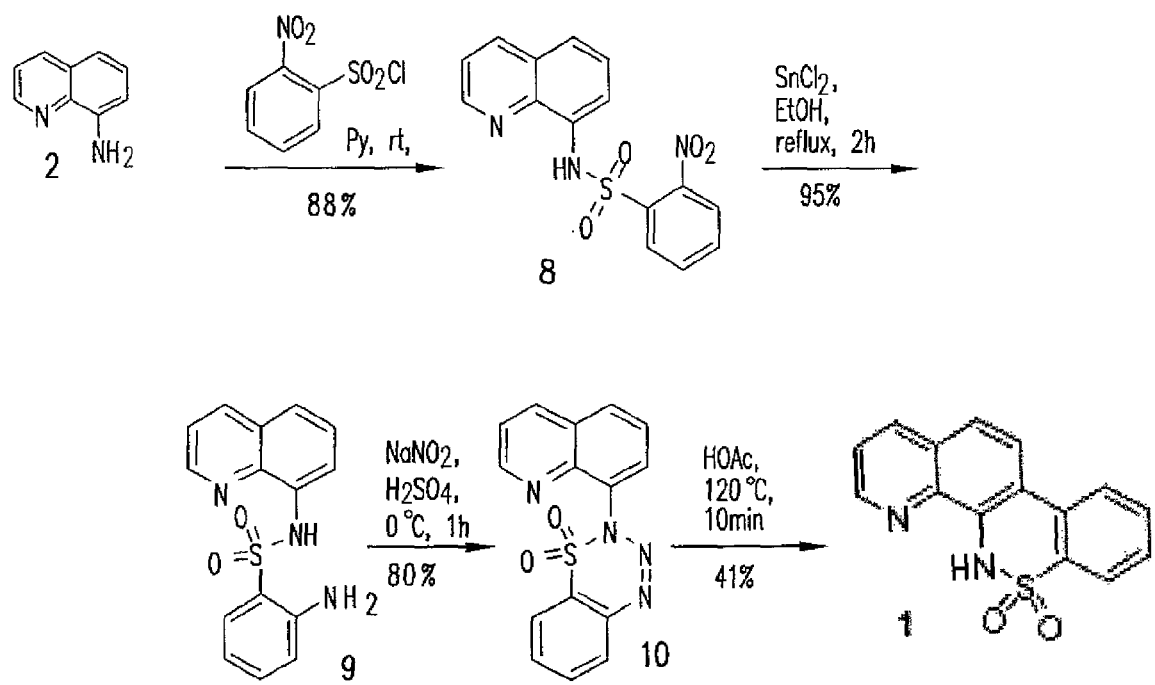
FIG. 2 depicts a method for synthesizing a particular compound of Formula II (the particular compound identified as compound 9) and a particular compound of formula III (the particular compound identified as compound 1).

The synthetic strategy was to generate N-8-quinolinyl benzenesulfonamides, and then construct the sultam skeleton through cyclization of the easily accessible N-8-quinolinyl benzenesulfonamides. Diazotization-induced cyclization was employed to synthesize the target compound (FIG. 2). Sulfonamide 8 was prepared from 2-nitrobenzenesulfonyl chloride and 8-aminoquinoline 2 in pyridine. The nitro group was reduced with $SnCl_2$ to provide amine 9 and subsequent diazotization afforded triazine 10. A procedure employing Cu (0) and NaOH (Ullman et al., 1911, Ber. Dtsch. Chem. Ges. 43:2694), failed to yield the desired product, but thermolysis in a variety of solvents (e.g. EtOH, $H_2O$, DMSO or HOAc) or neat afforded the product 1. The best result (41% yield) was obtained by heating in glacial acetic acid at 120° C. for ten minutes.

A second synthetic method involves a one-pot synthesis of N-8-quinolinyl benzenesultams from N-8-quinolinyl-2-aminobenzenesulfonamides. In a typical reaction, as shown in FIG. 3A, 2-aminobenzenesulfonamide 9a, prepared from 6-methoxy-2-methylquinolin-8-amine 2a (Qiu et al., 2007, Inorg. Chim. Acta. 360:431), was dissolved in HOAc and treated with 1.5 equiv of t-BuONO at 10° C. The reaction was allowed to warm to room temperature over 10 minutes and afforded sultam 1a in (78% yield) without isolation of the triazine intermediate.

A selection of N-8-quinolinyl-2-aminobenzenesulfonamides (9a-p) were prepared and subsequently cyclized in similar one-pot reactions to give sultams (1a-p) (FIG. 4). In each case, the product was isolated without intermediate purification (FIG. 4). Aminobenzenesulfonamides (9b-h and 9l-p) were synthesized in a similar manner described in FIG. 3A. Intermediates 9i-k were prepared from aniline 11 as outlined in FIG. 3B: Sulfonamidation of aniline 11 with 2-nitrobenzenesulfonyl chloride provided sulfonamide 12. Skraup reaction under modified conditions (Matsugi et al., 2000, Tetrahedron Lett. 41:8523) followed by reduction of nitro group provided the N-quinolinyl sulfonamides (9i-k).

A typical synthesis of a compound of Formulas II and III involves the following steps:

Compound 9a: To a solution of 6-methoxy-2-methylquinolin-8-amine 2a (0.19 g, 1.0 mmol) in pyridine (5 ml) was added 4-methyl-2-nitrobenzenesulfonyl chloride (0.24 g, 1.0 mmol). The mixture was stirred at room temperature overnight and precipitated with $H_2O$. The crude product was filtered and recrystallized from EtOH to afford nitrobenzenesulfonamide (0.31 g, 79%) as red crystal. $^1H$ NMR (300 MHz, $CDCl_3$) δ 10.1 (br, 1H); 8.04 (d, 1H), 7.86 (d, 1H), 7.62 (m, 2H), 7.39 (d, 1H), 7.24 (d, 1H), 6.73 (s, 1H), 3.88 (s, 3H), 2.66 (s, 3H), 2.41 (s, 3H); ESI-MS ($M^+$+1): 388.0. To a suspension of above nitro compound (0.20 g, 0.56 mmol) in EtOH (5 ml) was added $SnCl_2$ (0.32 g, 1.7 mmol) slowly. The mixture was refluxed for 2 h. After removal of EtOH, the residue was treated with 1M NaOH. The aqueous solution was extracted with $CH_2Cl_2$. The combined organic phases were washed by brine, dried over $Na_2SO_4$, and concentrated to yield 9a (0.18 g, 92%) as white solid. $^1H$ NMR (300 MHz, $CDCl_3$) δ 9.42 (br, 1H); 7.83 (d, 1H), 7.65 (d, 1H), 7.30 (s, 1H), 7.23 (d, 1H), 6.64 (s, 1H), 6.48 (d, 1H), 6.42 (s, 1H), 3.80 (s, 3H), 2.61 (s, 3H), 2.17 (s, 3H); ESI-MS ($M^+$+1): 358.1.

Compound 1a: To a solution of 9a (0.1 g, 0.28 mmol) in HOAc (1 ml) at 10° C. was added t-BuONO (0.05 mL, 0.42 mmol). The reaction was slowly warmed to room temperature over 10 min and quenched with $H_2O$. The mixture was extracted with EtOAc. The combined organic phases were washed with saturated $NaHCO_3$, dried over $Na_2SO_4$, and concentrated. Flash chromatography ($EtOAc/CH_2Cl_2$ 1:10 v/v) gave 1a (74 mg, 78%) as yellow solid. $^1H$ NMR (300 MHz, $CDCl_3$) δ 8.49 (s, 1H), 7.98 (d, 1H), 7.92 (d, 1H), 7.37 (d, 1H), 7.25 (d, 1H), 6.87 (s, 1H), 4.00 (s, 3H), 2.69 (s, 3H), 2.52 (s, 3H); $^{13}C$ NMR (75 MHz, $CDCl_3$) δ 156.2, 155.2, 142.2, 134.8, 134.5, 134.1, 132.2, 131.4, 130.1, 129.0, 126.8, 124.4, 122.0, 112.5, 100.0, 56.2, 25.2, 22.6; ESI-MS ($M^+$+1): 341.2.

In summary, a one-pot reaction for the conversion of N-8-quinolinyl-2-aminobenzenesulfonamides into their corresponding sultams under mild conditions has been described. This procedure offers access to a class of heterocyclic compounds that have shown therapeutic potential as novel BACE1 and NF-κB inhibitors, as described below.

Example 2

Inhibition of NFkB Activity

Small molecule regulation of signaling cascades associated with NFkB may provide novel approaches to alleviate numerous disease states. (D'Acquisto, et al., 2006 Curr. Opin. Pharmacol. 6:387; Gilmore, et al., 2006, Oncogene 25:6887). Several high-throughput campaigns in search of novel inhibitors of the NFkB signal transduction pathway have been undertaken. Two of these include a cell-based assay designed to identify IkBα stabilization, and a cell-based assay designed to identify inhibitors of TNFα-induced translocation of NFkB. Despite the differing assay design, cell type, and signal readout, a N-(quinolin-8-yl)benzenesulfonamide core scaffold was identified in both screens.

NFkB Inhibitory Assays

The first assay, an IkBα stabilization screen, was performed using a dual luciferase reporter system in the cell line OCILy3, an excellent model for primary tumors of the activated B-cell subtype (ABC) of diffuse large B-cell lymphoma (DLBCL) (FIG. 5A; PubChem AID: 445) (Davis, et al., 2007, Drug Dev. Technol. 5:85; Davis, et al., 2001, J. Exp. Med. 184:1861; Okamoto, et al., 2007, Curr. Pharm. Des. 13:447) Abnormally high constitutive NFkB activity levels have been noted in ABC-DLBCL, as in several types of cancer, due to high levels of IKKβ activity leading to elevated expression of NFkB targeted genes. (Okamoto, et al., 2007, Curr. Pharm. Des. 13:447) In this setting, IKK and proteasome activity produce high degradation of IkBα, liberating p50/65 and/or p50/c-Rel heterodimers to translocate to the nucleus. Because lines of ABC-DLBCL and other cancer types are dependent on constitutive NFkB activity, the NFkB pathway is a therapeutic target. This is particularly true for those processes governing IkBα degradation, and the therapeutic potential of small molecules for this purpose has been shown by studies in ABC-DLBCL lines using a specific IKKβ inhibitor. Furthermore, the use of an ABC-DLBCL line for a small-molecule screen of IkBα stabilization provides a context that is especially close to that of the targeted disease, with the potential that inhibitors may be found that affect specific upstream points in IKK activation.

To identify modulators of IkBα stability in ABC-DLBCL lines, such as small molecules inhibiting IKK or proteasome activity, changes in the level of an exogenous IkBα-luciferase fusion reporter expressed by an NFkB-insensitive promoter were measured. (Lam et al., 2005, Clin. Cancer res. 11:28; Ngo et al., 2006, Nature 441:106) The dual luciferase IkBα stabilization screen in OCI-Ly3 employed was designed to be suitable for HTS, by using IkBα fused to a green light-emitting beetle luciferase, with a red light-emitting beetle luciferase expressed in a native form to monitor cell uniformity and non-specific effects. (Davis, et al., 2007, Drug Dev. Technol. 5:85) Fold-responsiveness was further increased by having both reporters under the control of inducible promoters regulated by doxycycline. Upon doxycycline induction of both luciferase reporters, compounds that increased green luminescence with minimal effects on the red luminescence signal were scored as IkBα stabilizers. (Davis, et al., 2007, Drug Dev. Technol. 5:85).

The second assay, a translocation-based assay, was a high-content screen performed in human umbilical vein endothelial cells (HUVEC) using TNFα to stimulate nuclear translocation of endogenous NFkB (FIG. 5B; PubChem AID: 438). NFkB is sequestered in the cytoplasm due to its binding to IkBα, which blocks exposure of a nuclear localization sequence. Activation by cytokines such as TNFα results in proteasome degradation of IkBα and subsequent translocation of NFkB from the cytoplasm to the nucleus. In the assay, nuclear translocation of the endogenous p65 RelA subunit of NFkB, at 30 min post-stimulation, was monitored using fluorescent antibody detection and an automated imaging platform. (Mayer et al., 2006, Methods Enzyme 414:266) NFkB inhibitors in this assay, such as IkBα stabilizers, were detected as compounds that interfered with p65 translocation to the nucleus.

The above-described assays were validated using known inhibitors of the NFkB pathway (FIG. 6). The proteasome inhibitor MG-132 (1) 16 served as a positive control for the IkBα stabilization assay. The translocation assay used BAY 11-7082 (2), an agent that inhibits the TNFα-induced phosphorylation of IkBα. (Kamthong, 2001, Biochem 356:525; Izban et al., 2000, Hum. Pathol. 31:1482; Pierce et al., 1997, J. Biol. Chem. 272:21096). Additionally, a substituted 2-(thiophen-2-yl)quinazoline 3 which acts as an inhibitor of NFkB and $A\beta_1$ mediated transcriptional activation (Palanki et al., 2003, Bioorg. Med. Chem. Lett. 13:4077) was used as a positive control in a secondary assay that used TNFα to stimulate NFkB-dependent expression of a β-lactamase reporter (NFkB-bla in FIG. 7). This compound also served as a negative control for the dual luciferase IkBα stabilization assay.

Results

N-(quinolin-8-yl)benzenesulfonamide (4) and the related C7-locked N-(quinolin-8-yl)benzenesulfonamide (5) were identified as two common structures in both screens (FIG. 6). To further confirm that these agents interfered with the NFkB activation in a genuine manner, a reporter assay obtained from Invitrogen where induction of β-lactamase occurred in an NFkB-dependent manner was also performed on the active compounds. These data confirmed the ability of these compounds to inhibit the NFkB pathway, and the compounds were then advanced for further study (FIG. 7).

The synthesis of analogues of (4) was undertaken through a one-step process involving the addition of unsubstituted or 2-substituted, 6-substituted or 2,6-disubstituted quinolin-8-amines and a variety of sulfonyl chlorides (FIG. 7B). Amino-substituted analogues (19-22) (Izban et al., 2000, Hum. Pathol. 31:1482) were obtained by reduction of the corresponding nitro compounds with stannous chloride in ethanol (FIG. 7D). Over 40 novel analogues were prepared to establish preliminary structure-activity relationships.

Discussion

The synthesis of various analogues of (5) via a diazotization-induced cyclization of accessible N-8-quinolinyl-2-aminobenzenesulfonamides proved to be an efficient way of synthesizing this type of C7-locked sulfonamide (FIG. 7D).

Analogues of (4) and (5) were analyzed within both screens. Results for analogues of (4) are shown in FIG. 7A, while the results for derivatives of (5) are shown in FIG. 7C. In general, there was agreement in the relative potencies of analogues tested in both screening assays, as well as the NFkB β-lactamase reporter assay (although exceptions do exist).

A more rigid structure was associated with compound 5, because a bridge between the quinoline carbon 7 and the ortho-position of the sulfonyl phenyl ring locks the core scaffold in a rigid conformation. Two compounds (30 and 31) with the best overall potency values were identified here. Substituents at the 9 position (para to the sulfonylamide moiety designated R''' in FIG. 7C) are generally well tolerated as are 6-methoxy and 2-methyl substitutions (analogues 32 and 37-40, respectively).

Example 3

High- and Medium-Throughput Screening of Small Molecule Libraries to Identify Small Molecule Modulators of BACE1

A cell-based modified ELISA assay for measuring sAPPβ, the secreted ectodomain of β-amyloid precursor protein (APP) following β-secretase (BACE1) cleavage, was used to identify a class of compounds that interfered with the first step of sAPPβ generation. This assay has been described in International Application PCT/US2007/015938 (Published as International Publication No. WO 08/008,463), which is herein incorporated in its entirety for all purposes.

BACE1-mediated cleavage of APP is a key and necessary event in the generation of neurotoxic β-amyloid (Aβ), a widely accepted contributor to the development of Alzheimer's disease (AD). Studies in BACE1 knockout mice showed that they are viable, fertile, and do not produce Aβ, making BACE1 an attractive target for AD therapeutic intervention.

The SY5Y-BACEGFP-SEAPAPPwt cell based assay was developed to discover novel small molecule modulators of BACE1 activity. SY5Y cells were stably transfected with GFP-tagged BACE1 (BACE-GFP) and secreted alkaline phosphatase (SEAP)-tagged wildtype APP (SEAP-APPwt). BACE1 cleavage of SEAP-APPwt results in secretion into the media of SEAP-tagged sAPPβ, which is collected and specifically captured using an sAPPβ cleavage site-specific antibody (sβwt). After washing, the fluorescent alkaline phosphatase substrate 4-methylumbelliferyl phosphate (4-MUP) is used to detect the captured SEAP-sAPPβ (FIG. 8).

Targeted Screening Using N-(quinolin-8-yl)benzenesulfonamides and Related Compounds N-(quinolin-8-yl)benzenesulfonamides (FIG. 2) were recently reported as agents capable of down-regulating NF-κB activity (Xie et al., 2008). NF-κB is a ubiquitous transcription factor that is thought to play a role in many cellular processes, including immune and inflammatory responses, developmental processes, cellular growth, and apoptosis. Dysregulation of NF-κB signaling has been associated with many disease states, including asthma, arthritis, cancer, inflammatory conditions, neurodegenerative diseases, and heart disease (reviewed in Kumar et al., 2004). NF-κB inhibitors have also been reported to inhibit Aβ production (Paris et al., 2007). Furthermore, N-(quinolin-8-yl)benzenesulfonamides bear structural similarity to clioquinol and its second-generation compound PBT2. Both clioquinol and PBT2 are believed to be strong metal ion chelators that may interfere with oligomerization and aggregation of Aβ and promote its clearance (Ritchie et al., 2003). PBT2, developed by Prana Biotechnology, is currently in Phase II clinical trial for the treatment of AD. Thus, a small library of N-(quinolin-8-yl)benzenesulfonamides and related compounds was screened for agents that reduce BACE1-mediated cleavage of APP.

176 compounds were tested in the primary screen (FIG. 9). Briefly, each compound (10 mM stock in DMSO) was diluted 1:25 in DMSO and loaded onto 96-well plates to generate a 400 μM stock plate. 1 μl of each compound was then diluted 1:200 with cell culture media (0.5% DMSO concentration) in two separate 96-well plates for a final screening concentration of 2 μM. 150 μl of media containing compound was then transferred onto SY5Y-BACEGFP-SEAPAPPwt cells in 96-well format, and the BACE1 assay was performed as described previously. The primary screen was conducted in duplicate. A parallel screen was conducted at 10 μM concentration, also in duplicate. This data is not shown. Percent inhibition of the fluorescence signal was calculated as 100× [DMSO control−compound]/DMSO control The majority of data points were clustered between −25% and 25% inhibition of sAPPβ fluorescence signal (FIG. 9A). The Z' factors for all 4 96-well plates used in the primary screen were above 0.7 (data not shown). The threshold for hit selection was set at 3 standard deviations, or 59.76% inhibition, yielding 6 small molecule hits and a hit rate of 3.41% (FIG. 9B).

Several partial hits were also identified in the targeted screen of N-(quinolin-8-yl)benzenesulfonamides. Partial hits were defined loosely as compounds that either exhibited activity just below the threshold 59.76% inhibition in the 2 μM screen or those that displayed significant activity in the 10 μM screen. These compounds were characterized for 8-point dose-response and structure-activity relationship studies.

In summary, a cell-based BACE1 assay was used to screen N-(quinolin-8-yl)benzene-sulfonamides and related compounds, a class of NF-κB inhibitors. Because of their potency, availability, and the reported connection between NF-κB inhibition and Aβ generation, structural analogs of N-(quinolin-8-yl)benzenesulfonamides were also selected for investigation in structure-activity relationship studies. Primary and secondary screening using the cell-based BACE1 assay thus yielded chemotypes for SAR studies and further characterization in more physiological systems.

Example 4

Structure-Activity Relationship Studies and Characterization in Physiological Systems SAR studies were conducted for full and partial hits from the targeted screen of N-(quinolin-8-yl)benzenesulfonamides. Characterization in SY5Y-BACEGFP-SEAPAPPwt cells identified CU-264 as the most potent analog. CU-264 was further characterized in a of more physiological assay for its ability to reduce $A\beta_{40}$ and sAPPβ. CU-264 had the effect of raising $A\beta_{40}$ and sAPPβ levels.

SAR Studies of N-(quinolin-8-yl)benzenesulfonamides

Targeted screening of N-(quinolin-8-yl)benzenesulfonamides and related compounds revealed several full and partial hits capable of reducing the fluorescent signal from the cell-based BACE1 assay. Based on the chemical structures of the 176 compounds as well as the full and partial hits from the targeted screen, the structural elements that were critical for activity were identified. All full and partial hits contained the sulfonamide of quinoline motif either in open or cyclized varieties, as shown in FIG. 10. Substituting naphthalene for quinoline or removal of the sulfonamide substituent resulted in loss of activity.

28 full and partial hits were characterized in 8-point dose-response experiments for $IC_{50}$ determination in SY5Y-BACEGFP-SEAPAPPwt cells (FIG. 10). The investigation revealed 3 compounds with sub-micromolar potencies for sAPPβ reduction—CU-163, CU-264, and CU-262. Analysis of the data revealed a few structure-activity relationships. Addition of a methyl group at R3 resulted in a reduction of potency (compare CU-274, CU-278, CU-280, and CU-281 with CU-242, CU-271, CU-265, and CU-264, respectively). The electronic properties of the R groups did not affect compound activity based on the available data. The addition of electron-withdrawing, electron-donating, and electron-neutral groups did not have a clear and consistent effect on activity. Although there are no direct comparisons, cyclization of compounds (e.g. CU-262 and CU-282) did not significantly alter the potency compared with non-cyclized compounds (e.g. CU-264, CU-265, CU-280, and CU-281).

SAR studies of N-(quinolin-8-yl)benzenesulfonamides revealed 3 compounds with sub-micromolar potencies for sAPPβ reduction. The most potent compound, CU-264, is further evaluated.

Evaluation of CU-264 in More Physiological Systems

Figure 11:
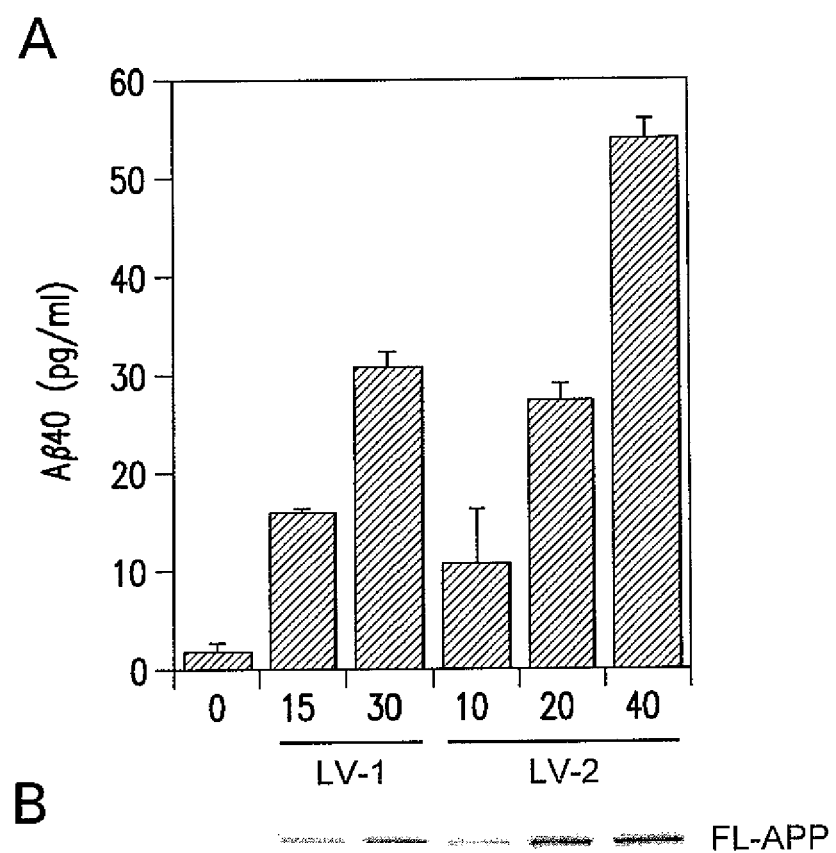

The previously described hit was further analyzed in physiologically relevant systems, e.g. primary neurons and Alzheimer's model mice. Two complementary neuronal cell systems were employed to test the effects of candidate compounds on various aspects of APP processing: cultured mouse cortical neurons (postnatal day 0) infected with recombinant lentivirus carrying human APPsw (Lenti-APPsw; FIG. 11); and cultured cortical neurons prepared from Tg2576 mice (carrying human APPsw transgene under the control of the PrP promoter). Lenti-APPsw infected cortical neurons can be prepared in a relatively large scale, but suffer from variability in lentiviral infection efficiency, resulting in variable levels of APP expression. In contrast, cortical neurons derived from Tg2576 provide constant APP expression. However, neuronal yield is generally much lower, since only half the pups will contain the transgene when heterozygote crossbreeds were conducted. Therefore, Initial characterization experiments were performed using cortical neurons infected with Lenti-APPsw. Compounds exhibiting inhibitory activity on sAPPβ and/or Aβ would then be re-evaluated in Tg2576 mice-derived neurons.

Ex vivo and in vivo assays will be used to characterize certain hit(s). Ex vivo systems, such as organotypic brain slices, offer an alternative to in vivo assays, and can also be used to test a large number of compounds. Furthermore, at least with regard to the Aβ release phenotype, brain slice data have been shown to correlate well with the results obtained in vivo (reviewed in Noraberg et al., 2005). Brain slices from p7 Tg2576 pups are used herein for compound characterization.

For in vivo studies, interstitial fluid (ISF) compound administration and Aβ measurement, as well as intraperitoneal (IP) compound injection, both utilizing Tg2576 mice, will be used to characterize compounds. Positioning of a guide cannula to the mouse hippocampus allows for insertion of a microdialysis apparatus, which can be used to infuse compounds at multiple concentrations sequentially in the awake mouse. Aβ measurements can be performed using the same apparatus, yielding rapid dose-response determinations (Cirrito et al., 2003). This method allows for rapid assessment of compound effect on Aβ on a dynamic time scale. More conventionally, compounds can also be administered via IP injection. For these experiments, 12-month old Tg2576 mice will be used.

CU-264 Does Not Reduce Aβ40 in Lenti-APPsw Infected Primary Cortical Neurons

Lenti-APPsw infected primary cortical neurons were used for the initial round of physiological experiments. Primary cortical neurons were harvested from wild-type P0 pups using established protocols. The majority of cells from the resulting culture exhibit neuronal morphology on light microscopy and express neuronal β-tubulin as visualized by immunocytochemistry using the TUJ1 antibody (Covance, FIG. 12).

The Lenti-APPsw vector was co-transfected into HEK293 T cells with ViraPower packaging mix (Invitrogen) to generate the lentivirus. Lentiviral-mediated transduction of APPsw in primary neurons was performed by adding neuron primary culture media containing the lentiviral particles to wild-type DIV-14 primary neurons (FIG. 11). After 24 hours, neurons were incubated with media for 72 hours prior to collecting for $A\beta_{40}$ measurement. Two batches of virus (LV-1 and LV-2) were tested, showing that there is batch-to-batch variation in the viral titer.

Using this experimental paradigm, CU-264 was tested at 10 and 2 µM concentrations to examine the sAPPβ- and Aβ-lowering activity of the compound. The protocol was modified slightly to allow for 24-hour compound treatment. DIV-14 wild-type primary neurons (FIG. 12) cultured on 6-well plates were incubated for 24 hours with primary culture media containing lentiviral particles. After infection, fresh media was mixed in a 1:1 ratio with conditioned media collected prior to lentiviral infection, and applied to the cells for 48 hours to allow for APP expression. At the end of this "pre-drug" incubation, media containing compound was applied for 24-hour treatment. Control experiments using DMSO alone showed that media collected after the 24-hour treatment period contained at least two times higher $A\beta_{40}$ than that collected just after the 48-hour pre-drug period. CU-264, which exhibited sub-micromolar potency for sAPPβ reduction in SY5Y-BACEGFP-SEAPAPPwt cells, did not reduce $A\beta_{40}$ in primary neurons (FIG. 13A). In contrast, CU-264 was observed to increase Aβ at 10 µM.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, GenBank Accession Numbers, and protocols are cited throughout this application, the disclosures of which are incorporated herein by reference in their entireties for all purposes.

What is claimed is:

1. A pharmaceutical composition comprising a compound of Formula III:

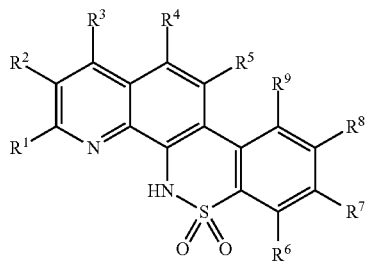

wherein $R^1$, $R^2$, $R^3$, $R^4$, $R^5$, $R^6$, $R^7$, $R^8$ and $R^9$ are independently selected for each occurrence from the group consisting of hydrogen, halogen, alkyl, aryl, alkoxy, aryloxy, alkylthiol, arylthiol, CN, OH, $CF_3$ and $NO_2$, wherein at least one of $R^1$ to $R^9$ is $CF_3$.

2. The composition of claim 1, wherein $R^1$, $R^2$, $R^3$, $R^4$, $R^5$, $R^6$, $R^7$, $R^8$ and $R^9$ are independently selected for each occurrence from the group consisting of hydrogen, methyl, Cl, $OCH_3$, $CF_3$, OH, and F.

3. A pharmaceutical composition comprising a therapeutically effective amount of a compound of claim 1 and a pharmaceutically acceptable carrier.

4. A pharmaceutical composition of claim 1, wherein the compound of formula III is:

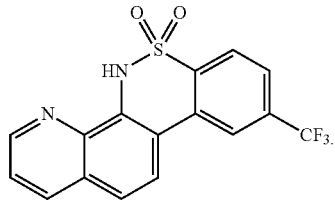 [SMILES: O=S1(=O)Nc2c(ccc3cccnc23)-c2cc(C(F)(F)F)ccc21]

* * * * *